(12) United States Patent
Sturmhoefel et al.

(10) Patent No.: US 7,011,833 B1
(45) Date of Patent: Mar. 14, 2006

(54) ENHANCING IMMUNE RESPONSES WITH B7-1 OR B7-2 IN THE ABSENCE OF A CROSSLINKING AGENT

(75) Inventors: Knut Sturmhoefel, Andover, MA (US); Stanley F. Wolf, Arlington, MA (US); Margot O'Toole, Newton, MA (US)

(73) Assignee: Genetics Institute, Inc., Cambridge, MA (US)

( * ) Notice: Subject to any disclaimer, the term of this patent is extended or adjusted under 35 U.S.C. 154(b) by 0 days.

(21) Appl. No.: 09/565,316

(22) Filed: May 5, 2000

Related U.S. Application Data

(60) Provisional application No. 60/132,944, filed on May 6, 1999.

(51) Int. Cl.
*A61K 39/395* (2006.01)
*A61K 38/17* (2006.01)
*C07K 14/705* (2006.01)

(52) U.S. Cl. .............................. 424/154.1; 424/134.1; 424/141.1; 424/142.1; 424/143.1; 424/144.1; 514/12; 514/21; 530/387.3; 530/388.1; 530/388.15; 530/388.22; 530/388.75; 530/350

(58) Field of Classification Search .......... 530/387.1, 530/387.3, 388.1, 388.15, 388.22, 388.75, 530/350; 514/8, 12, 514, 21; 424/130.1, 424/133.1, 134.1, 124.1, 192.1, 154.1, 141.1, 424/142.1, 143.1, 144.1

See application file for complete search history.

(56) References Cited

U.S. PATENT DOCUMENTS

| | | | |
|---|---|---|---|
| 5,116,964 A | * | 5/1992 | Capon et al. |
| 5,434,131 A | | 7/1995 | Linsley et al. |
| 5,580,756 A | | 12/1996 | Linsley et al. |
| 5,686,281 A | | 11/1997 | Roberts |
| 5,712,149 A | | 1/1998 | Roberts |
| 5,738,852 A | | 4/1998 | Robinson et al. |
| 6,071,716 A | | 6/2000 | Freeman et al. |
| 6,130,316 A | | 10/2000 | Freeman et al. |
| 6,149,905 A | | 11/2000 | Ostrand-Rosenberg et al. |

FOREIGN PATENT DOCUMENTS

| | | |
|---|---|---|
| WO | WO 95/06738 | 5/1995 |
| WO | WO 97/38711 | 10/1997 |
| WO | WO 00/06605 | 2/2000 |

OTHER PUBLICATIONS

Grewal and Flavell Annu. Rev. Immunol 1998; 16: 111-135.*
Coyle and Gutierrez-Ramos, Nature Immunol. 2001;2:203-209.*
Dunussi-Joannopoulos et al. Blood 1998, 96:617A.*
Chen, A. et al., "Non-glycosylated human B7-1(CD80) retains the capacity to bind its counter-receptors," *FEBS Lett.* May 29, 1998;428(3):127-34.
Corry, D.B. et al., "Differential effects of blockade of CD28-B7 on the development of Th 1 or Th2 effector cells in experimental leishmaniasis," *J. Immunol.*, Nov. 1, 1994; 153(9):4142-8.
Dellabona, P. et al., "Possible Use of Soluble Co-Stimulatory Molecules to Trigger Anti Tmour Immune Response In Vivo," *J. Cellular Biochemistry Suppl.*, Feb. 26-Apr. 17, 1994;18D:426.
Fields, P.E. et al., "B7.1 is a quantitatively stronger costimulus than B7.2 in the activation of naive CD8+ TCR-transgenic T cells," *J. Immunol.*, Nov. 15, 1998;161 (10):5268-75.
Freeman, G.J. et al., "B7-1 and B7-2 do not deliver identical costimulatory signals, since B7-2 but not B7-1 preferentially costimulates the initial production of IL-4," *Immunity*, May 1995;2(5):523-32.
Harding, F.A. et al., "CD28-B7 interactions allow the induction of CD8+ cytotoxic T lymphocytes in the absence of exogenous help," *J. Exp. Med.*, Jun. 1, 1993;177(6):1791-6.
Kuchroo, V.K. et al. "B7-1 and B7-2 costimulatory molecules activate differentially the Th1/Th2 developmental pathways: application to autoimmune disease therapy," *Cell*, Mar. 10, 1995;80(5):707-18.
Lenschow, D.J. et al., "Differential effects of anti-B7-1 and anti B7-2 monoclonal antibody treatment on the development of diabetes in the nonobese diabetic mouse," *J. Exp. Med.*, Mar. 1, 1995;181(3):1145-55.
McAdam, A.J. et al., The role of B7 co-stimulation in activation and differentiation of CD4+ and CD8+ T cells, *Immunol. Rev.*, Oct. 1998;165:231-47.
Moro, M. et al., "Induction of therapeutic T-cell immunity by tumor targeting with soluble recombinant B7-immunoglobulin costimulatory molecules," *Cancer Res.* Jun. 1, 1999;59(11):2650-6.
Rao, J.B. et al., "IL-12 is an effective adjuvant to recombinant vaccinia virus-based tumor vaccines: enhancement by simultaneous B7-1 expression," *J. Immunol.* May 1, 1996;156(9):3357-65.
Rennert, P. et al., "The IgV domain of human B7-2 (CD86) is sufficient to co-stimulate T lymphocytes and induce cytokine secretion," *Int. Immunol.* Jun. 1997;9(6):805-13.
Rulifson, I.C. et al., "CD28 costimulation promotes the production of Th2 cytokines," *J. Immunol.*, Jan. 15, 1997; 158(2):658-65.
Schweitzer, A.N. et al., "Role of costimulators in T cell differentiation: studies using antigen-presenting cells lacking expression of CD80 or CD86," *J. Immunol.*, Mar. 15, 1997;158(6):2713-22.

* cited by examiner

*Primary Examiner*—Phillip Gambel
*Assistant Examiner*—Ilia Ouspenski
(74) *Attorney, Agent, or Firm*—Lahive & Cockfield, LLP; Amy E. Mandragouras; Cynthia L. Kanik

(57) ABSTRACT

Methods of enhancing immune responses in which soluble forms of costimulatory molecules, e.g., B7 molecules, are administered to augment immune responses to antigens, e.g., to tumor cells and infectious agents are provided. The subject methods are useful for both prophylactic and therapeutic immunization of subjects.

34 Claims, 16 Drawing Sheets

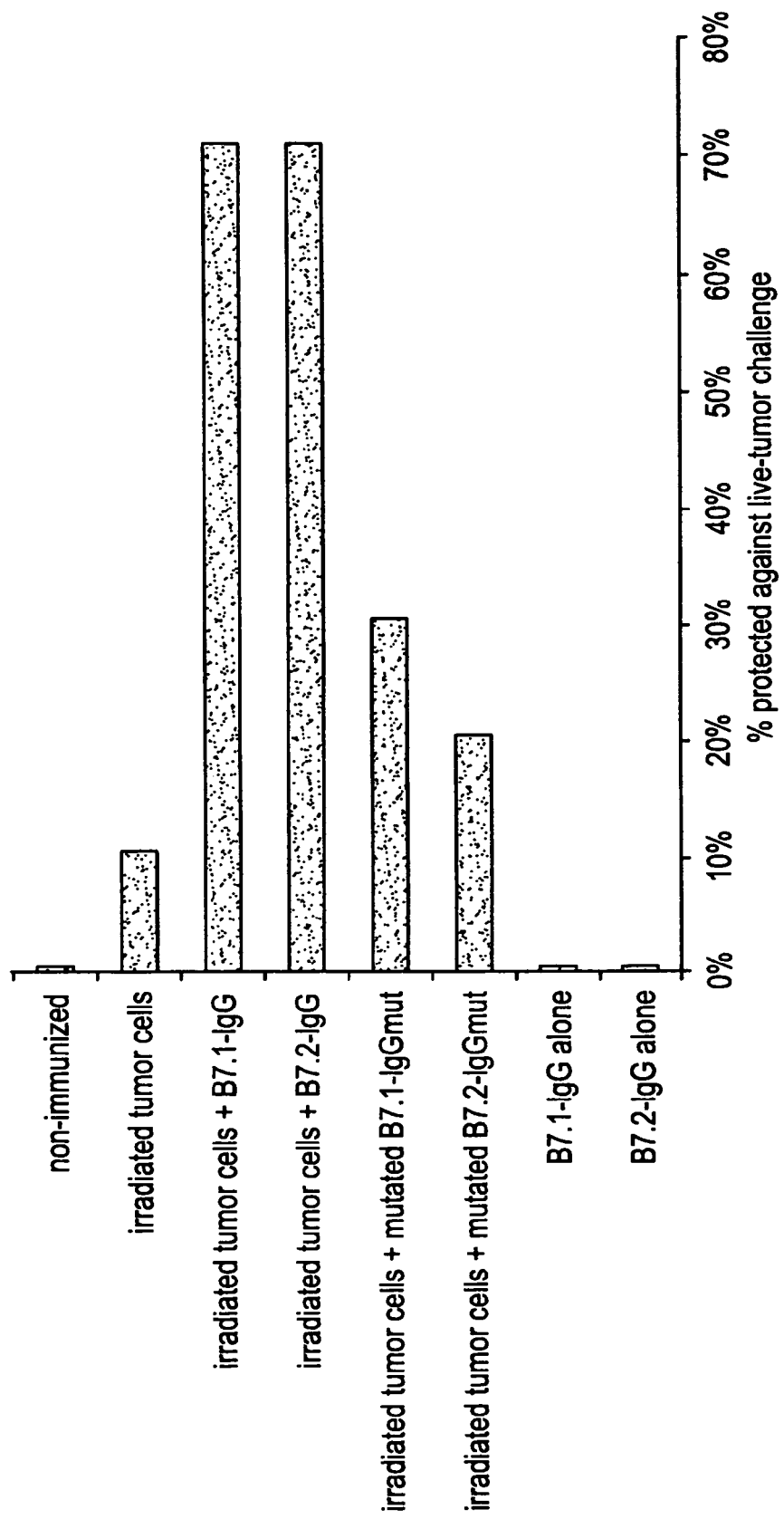

CD8 depleted untreated

CD8 depleted therapy with 50 μg B7.2-IgG

CD4 depleted untreated

CD4 depleted therapy with 50 μg B7.2-IgG wild-type Balb/c untreated

Balb/c IFNg KO non-immunized

Balb/c IFNg KO therapy with B7.2-IgG

Balb/c IFNg KO vaccination with irrad. MethA + B7.2-IgG

Balb/c wt non-immunized

Balb/c wt therapy with B7.2-IgG

Balb/c wt vacciantion with irrad. MethA + B7.2-IgG

ENHANCING IMMUNE RESPONSES WITH B7-1 OR B7-2 IN THE ABSENCE OF A CROSSLINKING AGENT

RELATED APPLICATION

This application claims priority to U.S. provisional application Ser. No. 60/132,944 filed on May 6, 1999, the contents of which is entirely incorporated herein by reference.

BACKGROUND OF THE INVENTION

In order for T cells to respond to foreign proteins, two signals must be provided by antigen-presenting cells (APCs) to resting T lymphocytes (Jenkins, M. and Schwartz, R. (1987) *J. Exp. Med.* 165, 302–319; Mueller, D. L., et al. (1990) *J. Immunol.* 144, 3701–3709). The first signal, which confers specificity to the immune response, is transduced via the T cell receptor (TCR) following recognition of foreign antigenic peptide presented in the context of the major histocompatibility complex (MHC). The second signal, termed costimulation, induces T cells to proliferate and become functional (Lenschow et al. 1996. *Annu. Rev. Immunol.* 14:233). Costimulation is neither antigen-specific, nor MHC restricted and is thought to be provided by one or more distinct cell surface molecules expressed by APCs (Jenkins, M. K., et al. 1988 *J. Immunol.* 140, 3324–3330; Linsley, P. S., et al. 1991 *J. Exp. Med* 173, 721–730; Gimmi, C. D., et al., 1991 *Proc. Natl. Acad. Sci. USA.* 88, 6575–6579; Young, J. W., et al. 1992 *J. Clin. Invest.* 90, 229–237; Koulova, L., et al. 1991 *J. Exp. Med.* 173, 759–762; Reiser, H., et al. 1992 *Proc. Natl. Acad. Sci. USA.* 89, 271–275; van-Seventer, G. A., et al. (1990) *J. Immunol.* 144, 4579–4586; LaSalle, J. M., et al., 1991 *J. Immunol.* 147, 774–80; Dustin, M. I., et al., 1989 *J. Exp. Med.* 169, 503; Armitage, R. J., et al. 1992 *Nature* 357, 80–82; Liu, Y., et al. 1992 *J. Exp. Med.* 175, 437–445). If T cells are only stimulated through the T cell receptor, without receiving an additional costimulatory signal, they become nonresponsive, anergic, or die, resulting in down modulation of the immune response.

The CD80 (B7-1) and CD86 (B7-2) proteins, expressed on APCs, are critical costimulatory molecules (Freeman et al. 1991. *J. Exp. Med.* 174:625; Freeman et al. 1989 *J. Immunol.* 143:2714; Azuma et al. 1993 *Nature* 366:76; Freeman et al. 1993. *Science* 262:909). B7-2 appears to play a predominant role during primary immune responses, while B7-1, which is upregulated later in the course of an immune response, may be important in prolonging primary T cell responses or costimulating secondary T cell responses (Bluestone. 1995. *Immunity.* 2:555).

One ligand to which B7-1 and B7-2 bind, CD28, is constitutively expressed on resting T cells and increases in expression after activation. After signaling through the T cell receptor, ligation of CD28 and transduction of a costimulatory signal induces T cells to proliferate and secrete IL-2 (Linsley, P. S., et al. 1991 *J. Exp. Med.* 173, 721–730; Gimmi, C. D., et al. 1991 *Proc. Natl. Acad. Sci. USA.* 88, 6575–6579; June, C. H., et al. 1990 *Immunol. Today.* 11, 211–6; Harding, F. A., et al. 1992 *Nature.* 356, 607–609). A second ligand, termed CTLA4 (CD152) is homologous to CD28 but is not expressed on resting T cells and appears following T cell activation (Brunet, J. F., et al., 1987 *Nature* 328, 267–270). In contrast to CD28, CTLA4 appears to be critical in negative regulation of T cell responses (Waterhouse et al. 1995. *Science* 270:985). Blockade of CTLA4 has been found to remove inhibitory signals, while aggregation of CTLA4 has been found to provide inhibitory signals that downregulate T cell responses (Allison and Krummel. 1995. *Science* 270:932).

There has been a long-felt need to develop methods of enhancing immune responses. For example, the immune response to certain viruses and to tumor cells has, to date, been difficult to augment using art recognized methods. Methods for enhancing immune responses in general, and in particular to enhance responses to tumor antigens and infectious agents (e.g., viral, bacterial, and/or parasite antigens), would be of great benefit.

SUMMARY OF THE INVENTION

The present invention provides methods for enhancing immune responses by manipulating the costimulatory pathway. The subject methods are particularly effective in augmenting responses to tumor antigens and antigens from infectious agents. The present invention is based, at least in part, on the discovery that soluble forms of costimulatory molecules can prophylactically and therapeutically enhance immune responses. This enhancement is seen despite the fact that the soluble costimulatory molecules of the invention are not administered on a solid phase (e.g., are not administered on a cell) and are administered in the absence of a cross-linking agent. These findings are particularly surprising in light of the teaching that soluble forms of B7-1 and B7-2 molecules fail to generate costimulatory responses (Hayden et al. 1996. Tissue Antigens. 48:242; U.S. Pat. No. 5,580,756).

Accordingly, in one aspect, the present invention provides methods of prophylactically enhancing an immune response by a subject to an antigen by administering a soluble composition comprising an extracellular domain of a costimulatory molecule, such that the immune response of the subject to the antigen is enhanced.

In another aspect, the invention provides methods of therapeutically enhancing an immune response by a subject to an antigen by administering a soluble composition comprising an extracellular domain of a costimulatory molecule, such that the immune response of the subject to the antigen is enhanced.

In one embodiment, the costimulatory molecule is selected from the group consisting of B7-1 and B7-2.

In another aspect, the invention provides a method of enhancing the CD8+ T cell response to a class I restricted antigen in a subject by administering a first agent comprising a class I restricted antigen or fragment thereof and a soluble composition comprising an extracellular domain of a B7 molecule, such that upon administration to the subject the CD8+ T cell response to a class I restricted antigen is enhanced.

In one embodiment, the methods further comprise administering a class II restricted antigen to the subject. In another embodiment, the methods further comprises administering an adjuvant to the subject.

In one embodiment, the B7 molecule is a B7-1 molecule. In another embodiment, the B7 molecule is a B7-2 molecule.

In one embodiment, the costimulatory molecule is monospecific. In another embodiment, the costimulatory molecule is dimeric and bivalent. In one embodiment, the soluble costimulatory molecule is monospecific and dimeric and bivalent.

In yet another embodiment of the invention, an extracellular portion of a B7 molecule is fused to a second protein or polypeptide comprising a portion of an immunoglobulin molecule. In one embodiment, the portion of the immunoglobulin molecule comprises cysteine residues. In one embodiment, the portion of the immunoglobulin molecule comprises the hinge, CH2 and CH3 regions of a human immunoglobulin molecule. In another embodiment, the portion of the immunoglobulin molecule comprises the hinge, CH 1, CH2 and CH3 regions of a human immunoglobulin molecule. In one embodiment, the immunoglobulin molecule has been modified to reduce complement fixation and/or Fc receptor binding.

In one embodiment, the antigen is a tumor cell antigen.

In another embodiment, the subject has a cancer of a type selected from the group consisting of: colon cancer, breast cancer, prostate cancer, renal cell cancer, leukemia, lymphoma, melanoma, mastocytoma, sarcoma, and bladder carcinoma.

In one embodiment, the antigen is an antigen selected from the group consisting of: a bacterial antigen, a viral antigen, and a parasite antigen.

In one embodiment, the immune response is a cellular immune response. In another embodiment, the immune response is a humoral immune response.

BRIEF DESCRIPTION OF THE DRAWINGS

FIG. 5A is a bar graph of the proliferative response, as determined by $^3$H-thymidine incorporation.

FIG. 6 is a bar graph of the protection against live tumor challenge conferred by immunization with irradiated P815 tumor cells alone or in combination with the indicated molecule. The results indicate that B7Ig is effective as an adjuvant in a prophylactic tumor vaccine model.

DETAILED DESCRIPTION

Figure 2:
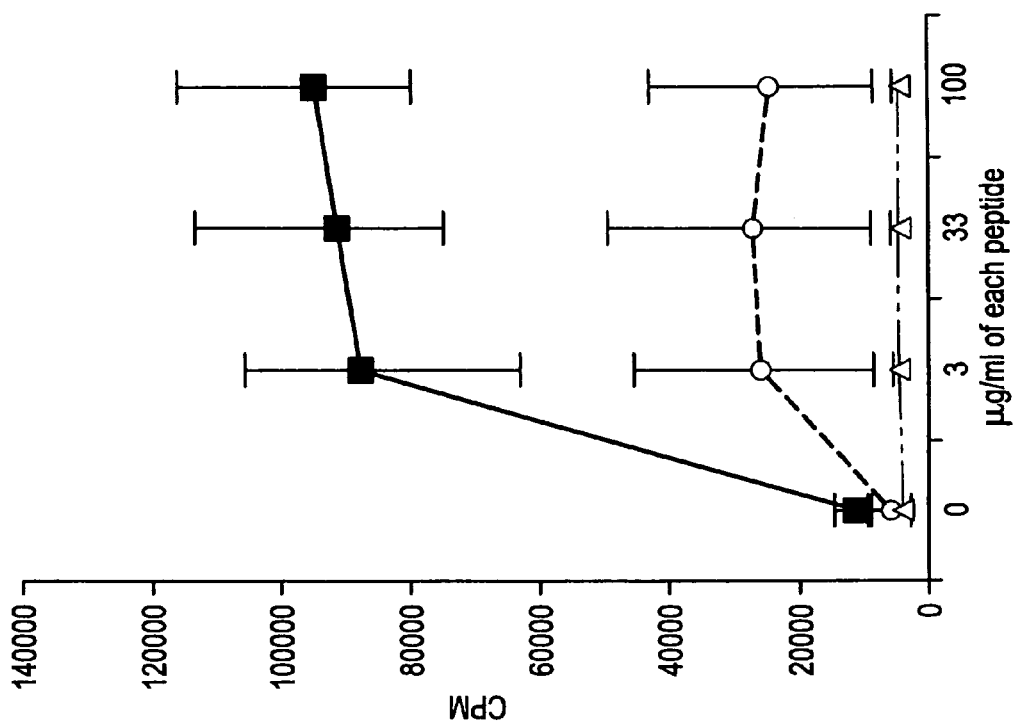
FIG. 2 is a line graph of the antigen specific proliferation of lymph node cells, as determined by $^3$H-thymidine incorporation, obtained from mice immunized with peptides alone (-O-), treated with B7-2Ig alone (-Δ-), or immunized with peptides and treated with B7-2Ig (-■-), and then re-immunized with peptides in the absence of B7-2Ig coadministration. The results indicate that cells from mice that had received a single B7-2Ig treatment at the time of primary immunization had greater proliferative responses following a second immunization than cells from mice that never received B7-2Ig. The data are from replicate experiments.

The instant invention provides improved methods of enhancing immune responses by administration of soluble costimulatory molecules (e.g., an extracellular domain of a B7 molecule, or a B7 fusion protein) to thereby enhance immune responses. The soluble costimulatory molecules are administered without a cross-linking agent, yet, surprisingly, stimulate T cell responses. In fact, Applicants have discovered that the instant methods result in an increased level of costimulation than costimulatory molecules presented on a surface, e.g., costimulatory molecules on the surface of a cell.

Before further description of the invention, certain terms employed in the specification, examples and appended claims are, for convenience, collected here.

Definitions

As used herein, the term "prophylactically" includes the administration of a costimulatory molecule prior to or simultaneously with exposure to the antigen against which the immune response is to be developed, augmented, and/or enhanced.

As used herein, the term "therapeutically" includes the administration of a costimulatory molecule to treat an existing or ongoing infection or disease (e.g., cancer or a viral or bacterial infection) which would benefit by treatment with a costimulatory molecule. For therapeutic treatment, a costimulatory molecule is administered at a point in time after exposure to the antigen against which the immune response is to be developed, augmented, and/or enhanced. It will be understood that therapeutic treatment with a costimulatory molecule may have other beneficial effects on the immune response of a subject, e.g., that are not specific for that particular antigen.

As used herein, the term "immune cell" includes cells that are of hematopoietic origin and play a role in an immune response. Immune cells include lymphocytes, such as B cells and T cells; natural killer cells; myeloid cells, such as monocytes, macrophages, eosinophils, mast cells, basophils, and granulocytes.

As used herein, the term "immune response" includes T and/or B cell responses, i.e., cellular and/or humoral immune responses. In one embodiment, the claimed methods can be used to reduce T helper cell responses. In another embodiment, the claimed methods can be used to reduce cytotoxic T cell responses. The claimed methods can be used to reduce both primary and secondary immune responses. The immune response of a subject can be determined by, for example, assaying antibody production, immune cell proliferation, the release of cytokines, the expression of cell surface markers, cytotoxicity, etc.

As used herein, the term "costimulate" with reference to activated immune cells includes the ability of a costimulatory molecule to provide a second, non-activating receptor mediated signal (a "costimulatory signal") that induces proliferation or effector function. For example, a costimulatory signal can result in cytokine secretion, e.g., in a T cell that has received a T cell-receptor-mediated signal. As used herein the term "costimulatory molecule" includes molecules which are present on antigen presenting cells (e.g., B7-1, B7-2, B7RP-1 (Yoshinaga et al. 1999. Nature 402: 827), B7h (Swallow et al. 1999. Immunity. 11:423) and/or related molecules (e.g., homologs)) that bind to costimulatory receptors (e.g., CD28, CTLA4, ICOS (Hutloff et al. 1999. Nature 397:263), B7h ligand (Swallow et al. 1999. Immunity. 11:423) and/or related molecules) on T cells. These molecules are also collectively referred to herein as "B7 molecules."

As used herein, the language "B7" or "B7 molecule" includes naturally occurring B7-1 molecules, B7-2 molecules, B7RP-1 molecules (Yoshinaga et al. 1999. Nature 402:827), B7h molecules (Swallow et al. 1999. Immunity. 11:423), structurally related molecules, fragments of such molecules, and/or functional equivalents thereof. The term "equivalent" is intended to include amino acid sequences encoding functionally equivalent costimulatory molecules having an activity of a B7 molecule, e.g., the ability to bind to the natural ligand(s) of B7 on immune cells, such as CTLA4, ICOS, and/or CD28 on T cells, and/or the ability to modulate immune cell costimulation.

As used herein, "polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, Proteins—Structure And Molecular Properties, $2^{nd}$ Ed., T. E. Creighton, W. H. Freeman and Company, New York (1993) and Wold, F., Posttranslational Protein Modifications: Perspectives and Prospects, pgs. 1–12 in Posttranslational Covalent Modification Of Proteins, B. C. Johnson, Ed., Academic Press, New York (1983); Seifter et al., Meth. Enzymol. 182:626–646 (1990) and Rattan et al., Protein Synthesis: Posttranslational Modifications and Aging, Ann. N.Y. Acad. Sci. 663: 48–62 (1992). Polypeptides may be branched or cyclic, with or without branching. Cyclic, branched and branched circular polypeptides may result from post-translational natural processes and may be made by entirely synthetic methods, as well.

As used herein, an "isolated polypeptide" or "isolated protein" refers to a polypeptide or protein that is substantially free of other polypeptides, proteins, cellular material and culture medium when isolated from cells or produced by recombinant DNA techniques, or chemical precursors or other chemicals when chemically synthesized. An "isolated" or "purified" polypeptide or biologically active portion thereof is substantially free of cellular material or other contaminating polypeptides from the cell or tissue source from which the B7 polypeptide is derived, or substantially free from chemical precursors or other chemicals when chemically synthesized. The language "substantially free of cellular material" includes preparations of B7 polypeptide in which the polypeptide is separated from cellular components of the cells from which it is isolated or recombinantly produced. In one embodiment, the language "substantially free of cellular material" includes preparations of B7 polypeptide having less than about 30% (by dry weight) of non-B7 polypeptide (also referred to herein as a "contaminating polypeptide"), more preferably less than about 20% of non-B7 polypeptide, still more preferably less than about 10% of non-B7 polypeptide, and most preferably less than about 5% non-B7 polypeptide. When the B7 polypeptide or biologically active portion thereof is recombinantly produced, it is also preferably substantially free of culture medium, i.e., culture medium represents less than about 20%, more preferably less than about 10%, and most preferably less than about 5% of the volume of the polypeptide preparation.

The language "substantially free of chemical precursors or other chemicals" includes preparations of B7 polypeptide in which the polypeptide is separated from chemical precursors or other chemicals that are involved in the synthesis of the polypeptide. In one embodiment, the language "substantially free of chemical precursors or other chemicals" includes preparations of B7 polypeptide having less than about 30% (by dry weight) of chemical precursors or non-B7 chemicals, more preferably less than about 20% chemical precursors or non-B7 chemicals, still more preferably less than about 10% chemical precursors or non-B7 chemicals, and most preferably less than about 5% chemical precursors or non-B7 chemicals.

Preferred B7 nucleic acid molecules and polypeptides are "naturally occurring." As used herein, a "naturally-occurring" molecule refers to an B7 molecule having a nucleotide sequence that occurs in nature (e.g., encodes a natural B7 polypeptide). In addition, naturally or non-naturally occurring variants of these polypeptides and nucleic acid molecules which retain the same functional activity, e.g., the ability to modulate adaptation to stress and/or virulence in a microbe. Such variants can be made, e.g., by mutation using techniques that are known in the art. Alternatively, variants can be chemically synthesized.

As used herein the term "variant(s)" includes nucleic acid molecules or polypeptides that differ in sequence from a reference nucleic acid molecule or polypeptide, but retains its essential properties. Changes in the nucleotide sequence of the variant may or may not alter the amino acid sequence of a polypeptide encoded by the reference nucleic acid molecule. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, and/or deletions in any combination. A variant of a nucleic acid molecule or polypeptide may be naturally occurring, such as an allelic variant, or it may be a variant that is not known to occur naturally. Non-naturally occurring variants of nucleic acid molecules and polypeptides may be made by mutagenesis techniques, by direct synthesis, and by other recombinant methods known to skilled artisans.

For example, it will be understood that the B7 polypeptides described herein are also meant to include equivalents thereof. Such variants can be made, e.g., by mutation using techniques that are known in the art. Alternatively, variants can be chemically synthesized. For instance, mutant forms of B7 polypeptides which are functionally equivalent, (e.g., have the ability to bind to CTLA4 and/or CD28) can be made using techniques which are well known in the art. Mutations can include, e.g., at least one of a discrete point mutation which can give rise to a substitution, or by at least one deletion or insertion. For example, random mutagenesis can be used. Mutations can also be made by random mutagenesis or using cassette mutagenesis. For the former, (chemical, PCR, doped oligonucleotide synthesis) and that collection of randomly mutated molecules is subjected to selection or screening procedures. In the latter, discrete regions of a polypeptide, corresponding either to defined structural or functional determinants are subjected to saturating or semi-random mutagenesis and these mutagenized cassettes are re-introduced into the context of the otherwise wild type allele. In one embodiment, PCR mutagenesis can be used. For example, Megaprimer PCR can be used (O. H. Landt, 1990. Gene 96:125–128).

As used herein, the term "enhancing an immune response" includes increasing T and/or B cell responses, i.e., cellular and/or humoral immune responses, by treatment of a subject using the claimed methods. In one embodiment, the claimed methods can be used to enhance T helper cell responses. In another embodiment, the claimed methods can be used to enhance cytotoxic T cell responses. The claimed methods can be used to enhance both primary and secondary immune responses. Preferably, the claimed methods increase the immune response by a subject when compared to the immune response by an untreated subject or a subject not treated using the claimed methods. An increase in an immune response can be shown, e.g., by an increased response of immune cells from the subject to the antigen upon treatment with the claimed methods. The immune response of a subject can be determined using a variety of in vitro or in vivo measurements of immune cell activation, for example, assaying antibody production, immune cell proliferation, the release of cytokines, the expression of cell surface markers, cytotoxicity, etc.

As used herein, the term "soluble" includes molecules, e.g., costimulatory molecules, which are not cell associated. Soluble costimulatory molecules retain the function of the cell-associated molecules from which they are derived, i.e., they are capable of binding to their cognate ligands on T cells and mediating signal transduction via a CD28 and/or CTLA4 molecule on a T cell, however, they are in soluble form, i.e., are not membrane bound. Preferably, the soluble compositions comprise an extracellular domain of a B7 molecule.

As used herein, the term "extracellular domain of a costimulatory molecule" includes a portion of a costimulatory molecule which, in the cell-associated form of the costimulatory molecule, is extracellular. Preferably, the extracellular domain of a costimulatory molecule comprises an extracellular domain of a B7 molecule. A B7 extracellular domain includes the portion of a costimulatory molecule which mediates binding to CD28 and/or CTLA4. For example, the human B7-1 extracellular domain comprises from about amino acid 1 to about amino acid 208 of the mature form of B7-1 (SEQ ID NO:1) and the human B7-2 extracellular domain comprises from about amino acid 24 to about amino acid 245 of the mature form of B7-2 (SEQ ID NO:2). In one embodiment, a soluble costimulatory molecule comprises an extracellular domain of a B7 molecule and further comprises a signal sequence.

As used herein, the term "class I restricted antigen" includes antigens which bind to the major histocompatibility complex (MHC) class I groove and which are presented to T cells in the context of MHC class I molecules. Class I restricted antigens primarily stimulate CD8+ T cells. As used herein, the term "class II restricted antigen" includes antigens which bind to the MHC class II groove and are presented to T cells in the context of MHC class II molecules. Class II restricted antigens primarily stimulate CD4+ T cells.

As used herein, the term "adjuvant" includes agents which potentiate the immune response to an antigen. Adjuvants can be administered in conjunction with costimulatory molecules to additionally augment the immune response.

As used herein, the term "monospecific" includes soluble costimulatory molecules which have only one specificity, i.e., they specifically bind to their cognate ligand, e.g., CD28 or CTLA4 on T cells. Such monospecific agents have not been engineered to include additional specificities and, thus, do not bind in a targeted manner to other cell surface molecules. As used herein the term "oligospecific" includes soluble costimulatory molecules having more than one specificity, e.g., having an additional specificity for a molecule other than a B7 ligand, e.g., a specificity for a cell surface molecule, such as a tumor cell antigen or a T cell receptor. As used herein, the term "bivalent" includes soluble costimulatory molecules that have two binding sites for interaction with their cognate ligand, e.g., CD28 and/or CTLA4 per soluble costimulatory molecule. As used herein, the term "dimeric" includes soluble forms that are present as homodimers, i.e., as a unit comprised of two identical subunits which are joined together, e.g., by disulfide bonds. As used herein, the term "multimeric" includes soluble forms having more than two subunits.

II. Soluble Costimulatory Molecules

The B7 antigens are a family of costimulatory molecules found on the surface of B lymphocytes, professional antigen presenting cells (e.g., monocytes, dendritic cells, Langerhans cells) and cells which present antigen to immune cells (e.g., keratinocytes, endothelial cells, astrocytes, fibroblasts, oligodendrocytes). These costimulatory molecules bind either CTLA4, CD28, and/or ICOS on the surface of T cells or other known or as yet undefined receptors on immune cells. The members of this family of costimulatory molecules are capable of providing costimulation to activated T cells to thereby induce T cell proliferation and/or cytokine secretion.

Purification techniques for B7 molecules have been established, and, additionally, B7 genes (cDNA) have been cloned from a number of species, including human and mouse (see, for example, Freeman, G. J. et al. (1993) *Science* 262:909–911; Azuma, M. et al. (1993) *Nature* 366:76–79; Freeman, G. J. et al. (1993) *J. Exp. Med.* 178:2185–2192).

Nucleotide sequences of costimulatory molecules are known in the art and can be found in the literature or on a database such as GenBank. See, for example, B7-2 (Freeman et al. 1993 *Science.* 262:909 or GenBank Accession numbers P42081 or A48754); B7-1 (Freeman et al. *J. Exp. Med.* 1991. 174:625 or GenBank Accession numbers P33681 or A45803; CTLA4 (See e.g., Ginsberg et al. 1985. *Science.* 228:1401; or GenBank Accession numbers P16410 or 291929); and CD28 (Aruffo and Seed. *Proc Natl. Acad. Sci.* 84:8573 or GenBank Accession number 180091), ICOS (Hutloff et al. 1999. *Nature.* 397:263; WO 98/38216), and related sequences.

In addition to naturally occurring forms of costimulatory molecules, the term "costimulatory molecule" also includes non-naturally occurring forms, e.g., variants or mutant forms of costimulatory molecules which retain the function of a costimulatory molecule, e.g., the ability to bind to cognate counter receptor. For example, DNA sequences capable of hybridizing to DNA encoding a B7 molecule, under conditions that avoid hybridization to non-costimulatory molecule genes, (e.g., under conditions equivalent to 65° C. in 5×SSC (1×SSC=150 mM NaCl/0.15 M Na citrate)) can be used to make antiB7 antibodies. Alternatively, DNA sequences which retain sequence identity over regions of the nucleic acid molecule which encode protein domains which are important in costimulatory molecule function, e.g., binding to other costimultory molecules, can be used to produce costimulatory proteins which can be used as immunogens. Preferably, nonnaturally occurring costimulatory molecules have significant (e.g., greater than 70%, preferably greater than 80%, and more preferably greater than 90–95%) amino acid identity with a naturally occurring amino acid sequence of a costimulatory molecule extracellular domain.

To determine amino acid residues of a costimulatory molecule which are likely to be important in the binding of a costimulatory molecule to its counter receptor, amino acid sequences comprising an extracellular domains of costimulatory molecules of different species, e.g., mouse and human, can be aligned and conserved (e.g., identical) residues noted. This can be done, for example, using any standard alignment program, such as MegAlign (DNA STAR). Such alignment programs are described in more detail below. Such conserved or identical residues are likely to be necessary for proper binding of costimulatory molecules to their receptors and are, thus, not likely to be amenable to alteration.

For example, the regions of the B7-1 molecule which are important in mediating the functional interaction with CD28 and CTLA4 have been identified by mutation. Two hydrophobic residues in the V-like domain of B7-1, including the Y87 residue, which is conserved in all B7-1 and B7-2 molecules cloned from various species, were found to be critical (Fargeas et al. 1995. *J. Exp. Med.* 182:667). Using these, or similar, techniques amino acid residues of an extracellular domains of costimulatory molecules which are critical and, therefore, not amenable to alteration can be determined.

Using B7 cDNA molecules, peptides having an activity of B7 can be produced using standard techniques. Host cells transfected to express peptides can be any procaryotic or eucaryotic cell. For example, a peptide having B7 activity can be expressed in bacterial cells such as *E. coli*, insect cells (baculovirus), yeast, or mammalian cells such as Chinese hamster ovary cells (CHO) and NS0 cells. Other suitable host cells and expression vectors may be found in Goeddel, (1990) supra or are known to those skilled in the art. Examples of vectors for expression in yeast *S. cerivisae* include pYepSec1 (Baldari. et al., (1987) *Embo J.* 6:229–234), pMFa (Kurjan and Herskowitz, (1982) *Cell* 30:933–943), pJRY88 (Schultz et al., (1987) *Gene* 54:113–123), and pYES2 (Invitrogen Corporation, San Diego, Calif.). Baculovirus vectors available for expression of proteins in cultured insect cells (SF 9 cells) include the pAc series (Smith et al., (1983) *Mol. Cell Biol.* 3:2156–2165) and the pVL series (Lucklow, V. A., and Summers, M. D., (1989) *Virology* 170:31–39). Generally, COS cells (Gluzman, Y., (1981) *Cell* 23:175–182) are used in conjunction with such vectors as pCDM8 (Seed, B., (1987) *Nature* 329:840) for transient amplification/expression in mammalian cells, while CHO (dhfr-Chinese Hamster Ovary) cells are used with vectors such as pMT2PC (Kaufman et al. (1987), *EMBO J.* 6:187–195) for stable amplification/expression in mammalian cells. A preferred cell line for production of recombinant protein is the NS0 myeloma cell line available from the ECACC (catalog #85110503) and described in Galfre, G. and Milstein, C. ((1981) *Methods in Enzymology* 73(13):3–46; and *Preparation of Monoclonal Antibodies: Strategies and Procedures*, Academic Press, N.Y., N.Y). Vector DNA can be introduced into mammalian cells via conventional techniques such as calcium phosphate or calcium chloride co-precipitation, DEAE-dextran-mediated transfection, lipofectin, or electroporation. Suitable methods for transforming host cells can be found in Sambrook et al. (*Molecular Cloning: A Laboratory Manual,* 2nd Edition, Cold Spring Harbor Laboratory press (1989)), and other laboratory textbooks. When used in mammalian cells, the expression vector's control functions are often provided by viral material. For example, commonly used promoters are derived from polyoma, Adenovirus 2, cytomegalovirus and most frequently, Simian Virus 40.

Peptides having an activity of B7 expressed in mammalian cells or otherwise can be purified according to standard procedures of the art, including ammonium sulfate precipitation, fractionation column chromatography (e.g. ion exchange, gel filtration, electrophoresis, affinity chromatography, etc.) and ultimately, crystallization (see generally, "Enzyme Purification and Related Techniques", *Methods in Enzymology,* 22:233–577 (1971)).

B7 molecules for making the soluble B7 molecules for use in the instant methods can be derived from any mammalian species, and are preferably human. The nucleotide sequences of B7 molecules from several sources are known in the art. The complete DNA sequence of human B7-1 (CD80) has the GenBank accession number M27533 and was published by Freeman et al. in 1989 in J. Immunol. 143:2714. The complete cDNA sequence of human B7-2 (CD86) has the GenBank accession number L25259 and was published by Freeman et al. in Science in 1993. 262;9090 or Azuma et al. Nature. 1993. 366:76. (See also WO 96/40915 for the sequence of both B7-1 and B7-2). The nucleotide and amino acid sequences of human B7-1 and human B7-2 are also shown in SEQ ID NOs:1 and 2 (B7-1) and SEQ ID NOs:3 and 4 (B7-2). Alternatively, such a sequence can be determined by isolating a B7 nucleic acid molecule from a desired source based on the ability of the sequence to hybridize to the known, e.g., human B7 sequences. For example, B7 molecules can be detected by their ability to hybridize under high or low stringency conditions to a known nucleic acid molecule which encodes a peptide having B7 activity. Appropriate stringency conditions which promote DNA hybridization, for example, 6.0× sodium chloride/sodium citrate (SSC) at about 45° C., followed by a wash of 2.0×SSC at 50° C. are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions, at about 65° C. In preferred embodiments, the B7 molecules are human B7 molecules.

In one embodiment, the soluble costimulatory molecule is derived from a naturally occurring B7-1 or B7-2 molecule. Polypeptides having an activity of a B7 molecule, as described herein, and having a sequence which differs from a naturally occurring B7 molecule due to degeneracy in the genetic code can also be expressed in soluble form and are also within the scope of the invention. Such nucleic acids encode polypeptides which are functionally equivalent to B7, (e.g., a polypeptide having B7 activity) but differ in sequence from the sequence of B7-1 or B7-2 known in the art. For example, a number of amino acids are designated by more than one triplet. Codons that specify the same amino acid, or synonyms (for example, CAU and CAC are synonyms for histidine) may occur due to degeneracy in the genetic code. As one example, DNA sequence polymorphisms within the nucleotide sequence of a B7 molecule (especially those within the third base of a codon) may result in "silent" mutations in the DNA which do not affect the amino acid encoded. However, it is expected that DNA sequence polymorphisms that do lead to changes in the amino acid sequences of the B7 antigen will exist within a population. It will be appreciated by one skilled in the art that these variations in one or more nucleotides (up to about 3–4% of the nucleotides) of the nucleic acids encoding peptides having the activity of a novel B lymphocyte antigen may exist among individuals within a population due to natural allelic variation. Such nucleotide variations and resulting amino acid polymorphisms are also within the scope of the invention. Furthermore, there may be one or more isoforms or related, cross-reacting B7 molecules.

In addition to naturally occurring allelic variants, B7 molecules within the scope of the invention can be made using art recognized techniques. In another embodiment, a soluble costimulatory molecule is a modified form of B7-1 or B7-2 which retains the function of a B7 costimulatory molecule, i.e., is functionally identical. The DNA sequence of a B lymphocyte antigen can be modified by genetic techniques to produce proteins or polypeptides with altered amino acid sequences. Such sequences are considered within the scope of the present invention, where the expressed polypeptide is capable of binding to CTLA4 and/or CD28 and modulating T cell mediated immune responses and immune function.

For example, in one embodiment, mutations can be introduced into a DNA molecule by any one of a number of methods, including those for producing simple deletions or insertions, systematic deletions, insertions or substitutions of clusters of bases or substitutions of single bases, to generate variants or modified equivalents of B lymphocyte antigen DNA. For example, changes in B7-1 or B7-2 cDNA sequences, such as amino acid substitutions or deletions, are preferably obtained by site-directed mutagenesis. Site directed mutagenesis systems are well known in the art. Protocols reagents can be obtained commercially from Amersham International PLC, Amersham, U.K.

Modified polypeptides having an activity of a B7 molecule, i.e., the ability to bind to the natural ligand(s) of a B7 molecule and modulate T cell mediated immune responses, as evidenced by, for example, cytokine production and/or T cell proliferation by T cells that have received a primary activation signal are considered within the scope of the invention.

Another example of modification of a peptide having the activity of a B7 molecule is substitution of cysteine residues preferably with alanine, serine, threonine, leucine or glutamic acid residues to minimize dimerization via disulfide linkages. In addition, amino acid side chains of a peptide having B7 activity can be chemically modified. Another modification is cyclization of the peptide.

In order to enhance stability and/or reactivity, polypeptides having B7 activity can be modified to incorporate one or more polymorphisms in the amino acid sequence of the antigen resulting from any natural allelic variation. Additionally, D-amino acids, non-natural amino acids, or non-amino acid analogs can be substituted or added to produce a modified protein within the scope of this invention. Furthermore, the peptides can be modified using polyethylene glycol (PEG) according to the method of A. Sehon and co-workers (Wie et al., supra) to produce a peptide conjugated with PEG. In addition, PEG can be added during chemical synthesis of the peptide. Other modifications of the peptides include reduction/alkylation (Tarr in: *Methods of Protein Microcharacterization*, J. E. Silver ed., Humana Press, Clifton N.J. 155–194 (1986)); acylation (Tarr, supra); chemical coupling to an appropriate carrier (Mishell and Shiigi, eds, *Selected Methods in Cellular Immunology*, W H Freeman, San Francisco, Calif. (1980), U.S. Pat. No. 4,939, 239; or mild formalin treatment (Marsh (1971), *Int. Arch. of Allergy and Appl. Immunol.* 41:199–215).

Preferred B7 polypeptides have B7 activity and at least about 60% identity, preferably at least about 70% identity, and more preferably at least about 80% identity with a naturally occurring B7 amino acid sequence. Polypeptides having B7 activity and at least about 90%, preferably at least about 95%, and more preferably at least about 98–99% identity with naturally occurring B7 molecule are also within the scope of the invention. The term amino acid "identity" at a given position refers to two peptides having the same amino acids at corresponding positions when the amino acid sequences of the peptides are aligned. When a position in the compared sequences is occupied by the same amino acid, then the molecules are identical at that position. A degree (or percentage) of identity between sequences is a function of the number of matching or identical positions shared by the sequences.

One of ordinary skill in the art can readily align two amino acid sequences to provide a biologically meaningful alignment. The comparison of sequences and determination of percent identity between two sequences can also be accomplished using a mathematical algorithm. In one embodiment, the percent identity between two amino acid sequences is determined using the Needleman and Wunsch (*J. Mol. Biol.* (48):444–453 (1970)) algorithm which has been incorporated into the GAP program in the GCG software package, using either a Blossom 62 matrix or a PAM250 matrix, and a gap weight of 16, 14, 12, 10, 8, 6, 5, or 4 and a length weight of 1, 2, 3, 4, 5, or 6. In yet another embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to B7 protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used. See, e.g., the NCBI web site.

"At least a portion of an extracellular domain of a B7 molecule" is defined as an amino acid sequence comprising entire extracellular domain sequence of B7 or a portion thereof which encodes a polypeptide having an activity (i.e., the ability to bind to the natural ligand(s) of B7 on immune cells, such as binding to CTLA4 and/or CD28 on T cells). A peptide having B7 activity binds CTLA4 and/or CD28 and modulates a T cell mediated immune response, as evidenced by, for example, binding to these ligands or by inducing cytokine production and/or proliferation by T cells that have received a primary activation signal as shown in the appended Examples. In a preferred embodiment, "at least a portion of an extracellular domain of a B7 molecule" includes a polypeptide comprising the entire extracellular portion of a human B7 antigen (e.g., approximately amino acid residues 1–208 of the sequence of B7-1 or approximately amino acids 24–245 of the sequence of B7-2) which can be used to bind CTLA4 and/or CD28.

In addition to B7 polypeptides comprising only naturally-occurring amino acids, B7 peptidomimetics are also provided. Peptide analogs are commonly used in the pharmaceutical industry as non-peptide drugs with properties analogous to those of the template peptide. These types of non-peptide compound are termed "peptide mimetics" or "peptidomimetics" (Fauchere, J. (1986) Adv. Drug Res. 15: 29; Veber and Freidinger (1985) TINS p. 392; and Evans et al. (1987) J. Med. Chem 30: 1229, which are incorporated herein by reference) and are usually developed with the aid of computerized molecular modeling.

Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biological or pharmacological activity), such as B7, but have one or more peptide linkages optionally replaced by a linkage selected from the group consisting of: —CH2NH—, —CH2S—, —CH2—CH2—, —CH=CH— (cis and trans), —COCH2—, —CH(OH)CH2—, —CH2SO—, by methods known in the art and further described in the following references: Spatola, A. F. in "Chemistry and Biochemistry of Amino Acids, Peptides, and Proteins," B. Weinstein, eds., Marcel Dekker, New York, p. 267 (1983); Spatola, A. F., Vega Data (March 1983), Vol. 1, Issue 3, "Peptide Backbone Modifications" (general review); Morley, J. S., Trends Pharm Sci (1980) pp. 463–468 (general review); Hudson, D. et al., Int J Pept Prot Res (1979) 14:177–185 (—CH2NH—, CH2CH2—); Spatola, A. F. et al., Life Sci (1986) 38:1243–1249 (—CH2—S); Hann, M. M., J Chem Soc Perkin Trans I (1982) 307–314 (—CH—CH—, cis and trans); Almquist, R. G. et al., J Med Chem (1980) 23:1392–1398 (—COCH2—); Jennings-White, C. et al., Tetrahedron Lett (1982) 23:2533 (—COCH2—); Szelke, M. et al., European Appln. EP 45665 (1982) CA: 97:39405 (1982)(—CH(OH)CH2—); Holladay, M. W. et al., Tetrahedron Lett (1983) 24:4401–4404 (—C(OH)CH2—); and Hruby, V. J., Life Sci (1982) 31:189–199 (—CH2—S—); each of which is incorporated herein by reference. A particularly preferred non-peptide linkage is —CH2NH—.

Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) to which the peptidomimetic binds to produce the therapeutic effect. Derivitization (e.g., labelling) of peptidomimetics should not substantially interfere with the desired biological or pharmacological activity of the peptidomimetic.

Systematic substitution of one or more amino acids of an B7 amino acid sequence with a D-amino acid of the same type (e.g., D-lysine in place of L-lysine) may be used to generate more stable peptides. In addition, constrained peptides comprising an B7 amino acid sequence or a substantially identical sequence variation may be generated by methods known in the art (Rizo and Gierasch (1992) Ann. Rev. Biochem. 61: 387, incorporated herein by reference); for example, by adding internal cysteine residues capable of forming intramolecular disulfide bridges which cyclize the peptide.

Those of skill in the art can, without undue experimentation, produce polypeptides corresponding to B7 peptide sequences and sequence variants thereof. Such polypeptides may be produced in prokaryotic or eukaryotic host cells by expression of polynucleotides encoding an B7 peptide sequence, frequently as part of a larger polypeptide. Alternatively, such peptides may be synthesized by chemical methods. Methods for expression of heterologous polypeptides in recombinant hosts, chemical synthesis of polypeptides, and in vitro translation are well known in the art and are described further in Maniatis et al., Molecular Cloning: A Laboratory Manual (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Merrifield, J. (1969) J. Am. Chem. Soc. 91: 501; Chaiken I. M. (1981) CRC Crit. Rev. Biochem. 11: 255; Kaiser et al. (1989) Science 243: 187; Merrifield, B. (1986) Science 232: 342; Kent, S. B. H. (1988) Ann. Rev. Biochem. 57: 957; and Offord, R. E. (1980) Semisynthetic Proteins, Wiley Publishing, which are incorporated herein by reference).

Peptides can be produced, e.g., by direct chemical synthesis. Peptides can be produced as modified peptides, with nonpeptide moieties attached by covalent linkage to the N-terminus and/or C-terminus. In certain preferred embodiments, either the carboxy-terminus or the amino-terminus, or both, are chemically modified. The most common modifications of the terminal amino and carboxyl groups are acetylation and amidation, respectively. Amino-terminal modifications such as acylation (e.g., acetylation) or alkylation (e.g., methylation) and carboxy-terminal-modifications such as amidation, as well as other terminal modifications, including cyclization, may be incorporated into various embodiments of the invention. Certain amino-terminal and/or carboxyl-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others.

The invention also provides B7 chimeric or fusion polypeptides. As used herein, an B7 "chimeric polypeptide" or "fusion polypeptide" comprises an B7 polypeptide operatively linked to a non-B7 polypeptide. An "B7 polypeptide" refers to a polypeptide having an amino acid sequence corresponding to B7 polypeptide, whereas a "non-B7 polypeptide" refers to a polypeptide having an amino acid sequence corresponding to a polypeptide which is not substantially homologous to the B7 polypeptide, e.g., a polypeptide which is different from the B7 polypeptide and which is derived from the same or a different organism. Within an B7 fusion polypeptide the B7 polypeptide can correspond to all or a portion of an B7 polypeptide. In a preferred embodiment, an B7 fusion polypeptide comprises at least one biologically active portion of an B7 polypeptide. Within the fusion polypeptide, the term "operatively linked" is intended to indicate that the B7 polypeptide and the non-B7 polypeptide are fused in-frame to each other. The non-B7 polypeptide can be fused to the N-terminus or C-terminus of the B7 polypeptide.

Preferred nucleic acid fragments encode B7 polypeptides of at least about 40 amino acid residues in length, preferably at least about 80 amino acid residues and length, and more preferably at least about 120 amino acid residues in length. Particularly preferred fragments are at least about 200 amino acids in length, e.g, comprise an entire extracellular domain of a B7 molecule. A number of processes can be used to generate fragments of an isolated DNA sequence. Small subregions or fragments of the nucleic acid encoding the B7-1 or B7-2 proteins, for example 1–30 bases in length, can be prepared by standard, synthetic organic chemical means. The technique is also useful for preparation of primers for use in the generation of larger synthetic fragments of B7 DNA.

Larger subregions or fragments of the genes encoding B lymphocyte antigens can be expressed as peptides by synthesizing the relevant piece of DNA using the polymerase chain reaction (PCR) (Sambrook, Fritsch and Maniatis, 2 *Molecular Cloning; A Laboratory Manual*, Cold Spring Harbor, N.Y., (1989)), and ligating the thus obtained DNA into an appropriate expression vector. Using PCR, specific sequences of the cloned double stranded DNA are generated, cloned into an expression vector, and then assayed for CTLA4/CD28 binding activity. For example, to express a secreted (soluble) form of the human B7-1 or B7-2 protein using PCR, a DNA can be synthesized which does not encode the transmembrane and cytoplasmic regions of the protein. This DNA molecule can be ligated into an appropriate expression vector and introduced into a host cell such as CHO, where the B7 protein fragment is synthesized and secreted. The B7 protein fragment can then readily be obtained from the culture media.

In one embodiment, a nucleic acid molecule encoding at least a portion of a B7 molecule, such as an extracellular domain portion which is lacking the transmembrane portion of the molecule is placed in an expression vector and is expressed by a host cell such that the B7 molecule is not expressed on the surface of the cell. For example, cDNA encoding an extracellular domain of a B7 molecule can be synthesized using the polymerase chain reaction (U.S. Pat. No. 4,683,202) using primers derived from the published sequence of B7-1 or B7-2 (see Freeman et al., J. Immunol. 1989. 143:2714 or Science. 1993. 262:9090). The resulting cDNA sequences can then be assembled into a eukaryotic or prokaryotic expression vector and the vector can be used to direct the synthesis of an extracellular domain of B7 by appropriate host cells, for example COS or CHO cells.

In another embodiment, the expression vector includes a DNA encoding a peptide having an activity of a B7 antigen and a DNA encoding a second polypeptide. The second polypeptide is preferably not derived from a costimulatory molecule. Preferably, a B7 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A B7-encoding nucleic acid molecule can be cloned into such an expression vector such that the fusion moiety is linked in-frame to the B7 protein. For example, hexa-histidine can be added to the peptide for purification by immobilized metal ion affinity chromatography (Hochuli, E. et al., (1988) *Bio/Technology* 6:1321–1325). In addition, to facilitate isolation of a B lymphocyte antigen free of irrelevant sequences, specific endoprotease cleavage sites can be introduced between the sequences of a fusion moiety and the peptide. It may be necessary to increase the solubility of a peptide by adding functional groups to the peptide, or by omitting hydrophobic regions of the peptide.

In one embodiment, DNA encoding a B7 molecule or portion thereof is linked in frame to DNA encoding an antigen to which an immune response is desired, e.g., a viral antigen or a tumor cell antigen.

In one embodiment, DNA encoding the amino acid sequence corresponding to an extracellular domain of a B7 antigen is joined to DNA encoding the amino acid sequences corresponding to the constant region of an immunoglobulin molecule (See e.g., U.S. Pat. No. 5,580,756 or WO 97/28267). The second peptide can include an immunoglobulin constant region, for example, a human Cγ1 domain or Cγ4 domain or Cμ or portion thereof (e.g., the hinge, CH2 and CH3 regions of human IgCγ1, or human IgCγ4, see e.g., Capon et al. U.S. Pat. No. 5,116,964, incorporated herein by reference). A resulting B7Ig fusion protein may have altered solubility, binding affinity, stability and/or valency (i.e., the number of binding sites available per molecule) and may increase the efficiency of protein purification.

In a preferred embodiment, the cysteine residues in the immunoglobulin constant region are conserved to allow for disulfide bonding and the formation of soluble dimeric B7Ig proteins. In one embodiment, a portion of a B7 molecule is fused to the constant region of an IgM antibody or portion thereof, to allow the formation of soluble multimeric forms of B7Ig proteins.

Particularly preferred B7Ig fusion proteins include an extracellular domain portion or variable region-like domain of human B7-1 or B7-2 coupled to an immunoglobulin constant region. The immunoglobulin constant region used in the soluble B7 molecule may contain genetic modifications which reduce or eliminate effector activity inherent in the immunoglobulin structure (see e.g., WO 97/28267). For example, DNA encoding an extracellular portion of B7-1 or B7-2, as well as DNA encoding the variable region-like domain of B7-1 or B7-2 or the constant region-like domain of B7-1 or B7-2 can be joined to DNA encoding the hinge, CH2 and CH3 regions of human IgCγ1 and/or IgCγ4 modified by site directed mutagenesis.

If a non-human immunoglobulin constant region is used, preferably the constant region is humanized. Techniques for preparing chimeric or humanized antibodies are well known in the art (see e.g., Morrison et al., *Proc. Natl. Acad. Sci. U.S.A.* 81:6851 (1985); Takeda et al., *Nature* 314:452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B, Teng et al., *Proc. Natl. Acad. Sci. U.S.A.*, 80:7308–7312 (1983); Kozbor et al., *Immunology Today*, 4:7279 (1983); Olsson et al., *Meth. Enzymol.*, 92:3–16 (1982); PCT Publication WO92/06193 and EP 0239400).

The techniques for assembling and expressing DNA encoding the amino acid sequences corresponding to B7 antigen and soluble B7Ig molecules, e.g., synthesis of oligonucleotides, PCR, transforming cells, constructing vectors, expression systems, and the like are well established in the art.

B7 fusion proteins and polypeptides produced by recombinant techniques may be secreted and isolated from a mixture of cells and medium containing the protein or peptide. Alternatively, the protein or peptide may be retained cytoplasmically and the cells harvested, lysed and the protein isolated. A cell culture typically includes host cells, media and other ingredients. Suitable media for cell culture are well known in the art. Protein and polypeptides can be isolated from cell culture medium, host cells, or both using techniques known in the art for purifying proteins and peptides. Techniques for transfecting host cells and purifying proteins and peptides are described in further detail herein.

III. Screening Structurally Related Soluble Costimulatory Molecules for Activity Screening structurally related B7 molecules for those which retain a characteristic B lymphocyte antigen activity as described herein can be accomplished using one or more of several different assays. For example, the peptides can be screened to see that they maintain specific reactivity with an anti-B7 monoclonal antibody that binds to a naturally occurring B7 molecule. Specifically, appropriate cells, such as COS cells, can be transfected with a DNA encoding a polypeptide to be tested. Production of secreted forms of B7 can be evaluated using anti-B7 monoclonal antibody or CTLA4Ig or CD28 fusion protein in an immunoprecipitation assay. The ability of cells expressing a peptide of interest to bind to CTLA4 or CD28 on plates by panning can also be tested. Alternatively, the ability of a test peptide to compete with a naturally occurring B7 molecule for binding to CD28 or CTLA4 can also be tested.

Other, more preferred, assays test the functional characteristics of the B7 antigen. As previously set forth, the ability of T cells to synthesize cytokines depends not only on occupancy or cross-linking of the T cell receptor for antigen (the "primary activation signal" provided by, for example anti-CD3, or phorbol ester to produce an "activated T cell"), but also on the induction of a costimulatory signal, in this case, by interaction with a B lymphocyte antigen, e.g. B7-1 or B7-2 with CD28 and/or CTLA4 molecules on the T cell. The binding of B7 molecules to their natural ligand(s) on T cells that have received signal one via the T cell receptor, has the effect of transmitting a signal to the T cell that induces the production of increased levels of cytokines, particularly of interleukin-2, which in turn stimulates the proliferation of the T lymphocytes. Other assays for B7 function, thus, involve assaying for the synthesis of cytokines, such as interleukin-2, interleukin-4 or other cytokines, and/or assaying for T cell proliferation by CD28+T cells which have received a primary activation signal.

In vitro, T cells can be provided with a first or primary activation signal by contacting them with anti-T3 monoclonal antibody (e.g. anti-CD3) or phorbol ester or, more preferably, by antigen in association with class I or class II MHC molecules. T cells which have received a primary activation signal are referred to herein as activated T cells. B7 function is assayed by adding a source of B7 (e.g., cells expressing a peptide having B7 activity or a secreted form of B7) and a primary activation signal such as antigen in association with class I or class II MHC to a T cell culture and assaying for a functional result, e.g., assaying the culture supernatant for interleukin-2, gamma interferon, or other known or unknown cytokine. For example, any one of several conventional assays for interleukin-2 can be employed, such as the assay described in *Proc. Natl. Acad. Sci. USA,* 86:1333 (1989) the pertinent portions of which are incorporated herein by reference. A kit for an assay for the production of interferon is also available from Genzyme Corporation (Cambridge, Mass.). T cell proliferation can also be measured as described in the Examples below. Peptides that retain the characteristics of the B7 antigen as described herein may result in increased per cell production of cytokines, such as IL-2, by T cells and may also result in enhanced T cell proliferation when compared to a negative control in which a costimulatory signal is lacking.

IV. Methods of Administering Soluble Costimulatory Molecules

The subject compositions and/or agents described herein are administered to subjects in whom it is desirable to promote an immune response. In one embodiment, soluble B7 molecules are administered with an antigen prophylactically, e.g., prior to infection with a pathogen or to a subject who is free of cancer. In another embodiment, the subject soluble B7 molecules are administered therapeutically, e.g., to subjects who have a preexisting condition which would benefit from enhanced costimulation, e.g., a subject who has cancer or is infected with a pathogen.

In one embodiment, the subject costimulatory molecules are coadministered with an antigen preparation. An antigen can be a protein, a polysaccharide, a lipopolysaccharide, a lipopeptide, or it can be a combination of any of these. For example, the antigen can include a native protein or protein fragment, of a synthetic protein or protein fragment, or peptide; it can include glycoprotein, glycopeptide, lipoprotein, lipopeptide, nucleoprotein, nucleopeptide; it can include a peptide—peptide conjugate; or it can include a recombinant nucleic acid expression product.

In one embodiment, an antigenic preparation comprises a mixture of antigens, e.g., the antigen is administered in the form of irradiated cells (e.g., tumor cells or virally infected cells), viral particles, or a crude homogenate. In another embodiment a purified preparation of an antigenic peptide or a recombinant form of an antigenic peptide is administered to the subject e.g., a viral peptide or a tumor associated antigen. In one embodiment, an antigen preparation comprises an MHC class I restricted peptide. In another embodiment, an antigen preparation comprises an MHC class II restricted peptide. In another embodiment, an antigen preparation comprises a combination of a class I restricted peptide and a class II restricted peptide for administration to the subject.

In one embodiment, the antigen is administered by "genetic immunization." In this embodiment, a DNA expression vector encoding the peptide of interest is injected into the host animal, e.g., into the skin or into a muscle of the subject. The gene products are correctly synthesized and glycosylated, folded, and expressed by the subject. Using this method, antigens which are difficult to obtain in sufficient quantity or purity can be administered. In one embodiment, DNA is injected into muscles or delivered into the skin coated onto gold microparticles by a particle bombardment device, a "gene gun." Genetic immunization has been shown to induce specific humoral responses and cellular immune responses (See, e.g., Mor et al. 1995. J. Immunol. 155:2039; Xu and Liew. 1995. Immunology. 84:173; Davis et al. 1994. Vaccine. 12:1503).

The optimal course of administration of the soluble B7 molecules may vary depending upon the subject to be treated. For example, soluble B7 molecules can be administered with an antigen and/or can be administered alone prior to administration of an antigen, or can be administered alone for several days after administering an antigen. In one embodiment, soluble B7 molecules can be administered "genetically" by administering a nucleic acid molecule encoding a soluble B7 molecule or portion thereof. In yet another embodiment, a soluble B7 molecule and an antigen are administered in the form of a conjugate.

Dosage regima of administration of soluble B7 molecules may be adjusted to provide the optimum therapeutic response for each subject without undue experimentation. For example, antibody titers to an antigen or cellular immune responses (e.g., DTH responses (Puccetti et al. 1994. Eur. J. Immunol. 24:1446)) to an antigen can be measured to determine whether or not the subject is developing an immune response or is manifesting an enhanced immune response to the antigen and the dosage regimen can be adjusted accordingly.

The active agent or composition may also be administered parenterally or intraperitoneally. The agent can be administered, for example, intranasally, orally, intravenously, intramuscularly, subcutaneously or mucosally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injection include sterile aqueous solutions (where water soluble) or dispersions and sterile powders for the extemporaneous preparation of sterile injectable solutions or dispersion. A pharmaceutical composition of the invention can be formulated to be suitable for a particular route of administration. For example, in various embodiments, a pharmaceutical composition of the invention can be suitable for injection, inhalation or insufflation (either through the mouth or the nose), or for intranasal, mucosal, oral, buccal, parenteral, rectal, intramuscular, intravenous, intraperitoneal, and subcutaneous delivery.

The agent or composition will be sterile. In addition, they shall be stable under the conditions of manufacture and storage and shall be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, asorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating active composition or agent in the required amount in an appropriate solvent with one or a combination of ingredients enumerated above, as required, followed by filter sterilization. Generally, dispersions are prepared by incorporating the active compound (e.g., the costimulatory molecule and/or the antigen and any additional agent) into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (e.g., agent or composition) plus any additional desired ingredient from a previously sterile-filtered solution thereof. The agent or composition can be administered in a form suitable for use with a needleless injector device (such devices are known in the art (see, e.g., U.S. Pat. Nos. 5,383,851; 5,581,198; 5,846,233) for example as described in Mol Med 1998. 4:109.

When the active agent or composition is suitably protected, as described above, the protein may be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active agent or composition for the treatment of individuals.

As used herein "pharmaceutically acceptable carrier" includes, e.g., solvents, dispersion media, coatings, antibacterial and antifungal agents, isotonic and absorption delaying agents, and the like. The use of such media and agents for pharmaceutically active substances is well known in the art. Supplementary agents can also be incorporated.

The agents of the invention are administered to subjects in a biologically compatible form suitable for pharmaceutical administration in vivo to enhance immune responses. By "biologically compatible form suitable for administration in vivo" is meant a form of the protein to be administered in which any toxic effects are outweighed by the therapeutic effects of the agent. The term subject is intended to include living organisms in which an immune response can be elicited, e.g., mammals. Examples of subjects include humans, non-human primates, dogs, cats, mice, rats, and transgenic species thereof. Administration of a peptide having the activity of B7 molecule as described herein can be in any pharmacological form including a therapeutically active amount of soluble B7 peptide alone, soluble B7 peptide in combination with an antigen, and soluble B7 peptide in combination with a pharmaceutically acceptable carrier.

Administration of a therapeutically or prophylactically active amount of the compositions of the present invention is defined as an amount effective, at dosages and for periods of time necessary to achieve the desired result. Preferably the administration of a soluble B7 molecule (with or without an antigen) results in an enhanced immune response to an antigen (e.g., a viral or a tumor cell antigen).

The immune response to an antigen by a subject (e.g., a cellular and/or humoral immune response) can be measured using art recognized techniques. Measurements of immune responses to an antigen can be made in vivo or assayed in vitro. For example, immune cell reactivity to a tumor cell can be measured by performing a biopsy and looking for cellular infiltrates. In situ cytokine staining can be performed at sites of infection or near the site of a tumor or in draining lymph nodes. In vitro culturing of cells can be performed to test for cellular reactivity to an antigen (e.g., proliferation and/or cytokine production in the presence of the antigen and/or cytotoxic activity against the antigen). For example, a therapeutically or prophylactically active amount of a polypeptide having B7 activity may vary according to factors such as the disease state, age, sex, and weight of the individual, and the ability of the peptide to elicit a desired response in the individual. Dosage regima may be adjusted to provide the optimum therapeutic or prophylactic response. For example, several divided doses may be administered daily or the dose may be proportionally reduced as indicated by the exigencies of the therapeutic situation.

The active compound may be administered in a convenient manner such as by injection (subcutaneous, intravenous, etc.), oral administration, inhalation, transdermal application, or rectal administration. Depending on the route of administration, the active compound may be coated in a material to protect the compound from the action of enzymes, acids and other natural conditions which may inactivate the compound.

The invention further pertains to the active compound in the form of a medicament for use in therapy as described herein. The active compound may also be used in the manufacture of a medicament for use in therapy.

V. Administration of Additional Agents

The subject treatment may be supplemented with the administration of additional agents to further augment the immune response. For example, adjuvants and/or cytokines can be administered to a subject.

In one embodiment, cytokines such as: granulocyte-macrophage colony stimulating factor, macrophage colony stimulating factor, granulocyte colony stimulating factor, interleukin 1, interluekin 2, interleukin 3, interleukin 4, interleukin 5, interleukin 6, interleukin 7, interleukin 10, and/or interleukin 12 can be administered. Interferon, e.g., α, β, and/or gamma interferon can also be administered.

Preferably, cytokines such as IL-12 which favor the development of Th1-type T helper responses and the development of cellular immunity are administered. In another embodiment, an additional agent that modulates a costimulatory signal, e.g., an anti-CD28 antibody can be administered to the subject.

In another embodiment, agents which are known adjuvants can be administered. At this time, the only adjuvant widely used in humans has been alum (aluminum phosphate or aluminum hydroxide). Other adjuvants, e.g., saponin and its purified component Quil A, Freund's complete adjuvant and other adjuvants used in research and veterinary applications have potential use in human vaccines. However, new chemically defined preparations such as muramyl dipeptide, monophosphoryl lipid A, phospholipid conjugates such as those described by Goodman-Snitkoff et al. J. Immunol. 147:410–415 (1991) resorcinols, non-ionic surfactants such as polyoxyethylene oleyl ether and n-hexadecyl polyethylene ether, enzyme inhibitors include pancreatic trypsin inhibitor, diisopropylfluorophosphate (DEP) and trasylol can also be used. In embodiments in which antigen is administered, the antigen can e.g., be encapsulated within a proteoliposome as described by Miller et al., J. Exp. Med. 176:1739–1744 (1992) and incorporated by reference herein, or in lipid vesicles, such as Novasome™ lipid vesicles (Micro Vescular Systems, Inc., Nashua, N.H.), to further enhance immune respones.

The practice of the present invention will employ, unless otherwise indicated, conventional techniques of cell biology, cell culture, molecular biology, microbiology, recombinant DNA, and immunology, which are within the skill of the art. Such techniques are explained fully in the literature. See, for example, *Genetics; Molecular Cloning A Laboratory Manual*, 2nd Ed., ed. by Sambrook, J. et al. (Cold Spring Harbor Laboratory Press (1989)); *Short Protocols in Molecular Biology*, 3rd Ed., ed. by Ausubel, F. et al. (Wiley, NY (1995)); *DNA Cloning*, Volumes I and II (D. N. Glover ed., 1985); *Oligonucleotide Synthesis* (M. J. Gait ed. (1984)); Mullis et al. U.S. Pat. No. 4,683,195; *Nucleic Acid Hybridization* (B. D. Hames & S. J. Higgins eds. (1984)); the treatise, *Methods In Enzymology* (Academic Press, Inc., N.Y.); *Immunochemical Methods In Cell And Molecular Biology* (Mayer and Walker, eds., Academic Press, London (1987)); *Handbook Of Experimental Immunology*, Volumes I–IV (D. M. Weir and C. C. Blackwell, eds. (1986)); and Miller, J. *Experiments in Molecular Genetics* (Cold Spring Harbor Press, Cold Spring Harbor, N.Y. (1972)).

The contents of all references, pending patent applications and published patents, cited throughout this application are hereby expressly incorporated by reference. Each reference disclosed herein is incorporated by reference herein in its entirety. Any patent application to which this application claims priority is also incorporated by reference herein in its entirety.

The invention is further illustrated by the following examples, which should not be construed as further limiting.

EXAMPLES

Example 1

Soluble Costimulatory Molecules Enhance CTL Responses

Optimal T cell activation requires both signaling through the T cell receptor and co-stimulation. B7-1 and B7-2 are two potent co-stimulatory molecules on the surface of APCs. The effects of a soluble form of B7-2 on in vivo T cell responses have been examined. The soluble molecule is a chimeric protein containing the extra-cellular domain of B7-2 fused to the Fc region of mouse IgG2a. Administration of B7-2Ig fusion protein at the time of immunization with class II restricted peptides significantly enhanced antigen-specific T cell proliferation and cytokine responses. B7-2Ig administration also enhanced the CTL response to immunization with a class I-restricted peptide. Enhancement of the CTL response by B7-2Ig was significantly increased in the presence of a T helper cell response to class II-restricted peptides. These findings demonstrate the immune stimulatory activity of a soluble protein form of costimulatory molecules, e.g., B7-2 on multiple T cell immune response parameters and demonstrate that these molecules have clinical utility in infectious disease and vaccine indications.

Materials and Methods used in Example 1:

Mice

Female BALB/cJ mice (Jackson Labs, Bar Harbor, Me.) 7 to 10 weeks of age were used throughout this study.

Preparation of Peptide Immunogens

All peptides used were $H-2^d$-restricted immunodominant epitopes from nucleoprotein (NP) of influenza virus A/PR18/34. Class I-restricted peptide, aa 147–155, Thr Tyr Gln Arg Thr Arg Ala Leu Val (SEQ ID NO:5), (Taylor, P. M., et al. 1987, *Immunogenetics* 26:267) and class II-restricted peptides, aa 55–77, Arg Leu Ile Gln Asn Ser Leu Thr Ile Glu Arg Met Val Leu Ser Ala Phe Asp Glu Arg Arg Asn Lys —OH (SEQ ID NO:6), and aa 206–229, Phe Trp Arg Gly Glu Asn Gly Arg Lys Thr Arg Ile Ala Tyr Glu Arg Met Cys Asn Ile Leu Lys Gly Lys (SEQ ID NO:7), (Brett, S. J. et al. 1991, *Journal Immunology* 147:1647), were synthesized on the PE Biosystems 430A peptide synthesizer using standard Fmoc/NMP chemistry with HOBT/DCC amino acid activation. They were analyzed and purified on a Beckman HPLC and mass was confirmed using a Bruker MALDI mass spectrometer.

Preparation of AIPR18/34 Virus Stock

AIPR/8/34 influenza virus stock was prepared and titered by injection of seed virus at a dilution of 104 into 10 day embryonated chicken eggs. After 42 hr. of incubation, the allantoic fluids of infected eggs were individually harvested and sterility confirmed on blood agar plates. Sterile fluids were pooled, aliquots prepared and quick-frozen with storage at −70° C. Plaque titration (Bucher, D. J. et al. 1991, *J Clin Microbiol* 29:2484) was performed following quick-thawing and dilution of the virus (in allantoic fluid.)

B7-2Ig Fusion Protein

B7-2Ig fusion protein was expressed and purified as described previously (Fields, P. E., et al. 1998. *J Immunol* 161:5268). In brief, expression plasmid pED was constructed from cDNA encoding the signal and extracellular domains of murine B7-2 joined to the genomic DNA encoding the hinge, CH2, and CH3 regions of mouse IgG2a. The expression vector was transfected into a CHO cell line and amplified by previously described techniques (Kaufman, R. J., et al. 1988. *Journal of Biological Chemistry* 263:6352.). Concentrated cell culture supernatant was passed over a rProtein A Sepharose Fast Flow column (Pharmacia Biotech). B7-2Ig was eluted with 20 mM citrate pH 3.0, neutralized with 1M Tris (Sigma) pH 8.0, and formulated in PBS pH 7.2 by buffer exchange. Protein concentration was calculated using an absorbance at 280 nm and an extinction coefficient of 1.33 cm/mg/ml. Endotoxin levels were less than 0.25 EU/mg as determined by gel clot assay (Cape Cod Associates). The percentage of protein as multimer was less than 1% as determined by analysis using TSK 3000 SWXL column (Toso Haas USA, Mongomeryville, Pa.). In vitro co-stimulatory activity of B7-2Ig has been demonstrated (Fields, P. E., et al. 1998. *J Immunol* 161:5268). Experiments presented here have been performed at least three times with similar results. At least one of the replicates of each experiment was performed using purified mouse monoclonal IgG2a directed against an irrelevant human protein, GDF-9, (Genetics Institute, Cambridge Mass.) as a control for B7-2Ig treatment.

Peptide Immunization

100 µg of the indicated peptide or peptide mixture was mixed 1:1 by volume with IFA (Sigma) and emulsified. Mice were immunized subcutaneously with antigen/IFA emulsion in 100 µl at the base of the tail. B7-2Ig in 100 µl was administered subcutaneously at a site proximal to the peptide immunization site. In experiments where lymph node cells were harvested, mice received peptide and B7-2Ig as described above both at the base of the tail and at the back of the neck. Treatment groups consisted of 5 mice each. B7-2Ig was administered in 0.1% aluminum hydroxide (Rehydragel, Rehies, Dublin, Ireland).

Live Virus Immunization and Challenge

Metafane (Mallinckrodt Veterinary, Mundelein, Ill.) was administered by nose cone until mice lost reflex response. Live virus diluted in PBS was administered intra-nasally in a final volume of 40 µl. The lethal virus dose (4,000 PFU/mouse) caused 100% mortality in non-immunized mice. Immunization dose of 40 PFU/mouse caused no morbidity and resulted in complete protection from lethal challenge.

Proliferation Assays

Lymph nodes (excluding mesenteric nodes) and spleens were collected on the indicated days and single cell suspensions prepared and cultured in flat bottom 96 well plates at $5 \times 10^5$ cells/well in 200 µl in RPMI 1640 (Gibco/BRL), supplemented to contain $5 \times 10^{-5}$ M 2ME, 2 mM Lglutamine, 100 U/ml Penicillin and 100, µg/ml Streptomycin (Gibco/BRL), 10% FCS. Class II-restricted peptides were added at the start of culture at the indicated concentration. Proliferation was measured by 3H thymidine incorporation following an 18 hour pulse (1 µC/well) with a 1450 Microbeta Plate Reader (Wallac). Comparison of proliferative responses from lymph node cells on days 3, 5, 7, and 9 post primary immunization were conducted. Secondary responses were assessed from spleens harvested three days after secondary immunization.

Cytokine Assays

Cells were cultured as described above for proliferation assays. Supernatants were harvested on day 3 and levels of IFN-γ, IL-5 and IL-13 were determined by ELISA using commercially available kits (Genzyme, Cambridge Mass. for IFN-γ, Endogen, Woburn Mass. for IL-5, and R&D Systems, Minneapolis, Minn. for IL-13).

CTL Assay on Individual Unfractionated Mouse Blood Cell Samples

Two to three weeks following primary immunization, samples of blood (150 µl to 200 µl each) were collected by retro-orbital bleed from mice anesthetized with Aerrane, (Ohmeda Caribe, Inc, Guayama, PR). Samples were diluted with 100 µl PBS containing 50 U heparin. A 40 µl sample was removed for white blood cell counts. Differential counts on samples were not routinely performed. The percentage of lymphocytes in the white blood cell fraction was 69%+8% by differential count of 100 samples taken at various times during the study. Cells were washed to remove heparin.

A total of $8 \times 10^5$ WBC/mouse were re-suspended in 10 ml of media consisting of RPMI 1640 supplemented as described above for proliferation assay and, in addition, with the following supplements for the generation of primary in vitro CTL responses: 4 µg/ml anti-CD28 (PV 1.17) and 10 U/ml recombinant murine IL-12 (rmIL-12, Genetics Institute, Cambridge, Mass.), 10 U/ml IL-2 and 200 U/ml IL-6, (Genzyme, Cambridge, Mass.), 0.1 pM class I-restricted peptide (Thr Tyr Gln Arg Thr Arg Ala Leu Val, aa 147–155 (SEQ ID NO:5)), and $1 \times 10^6$/ml irradiated (2,000 rads) syngeneic spleen cells treated with 0.17 M NH4CL buffered with 0.017 M Tris to lyse RBCs (Gajewski, T. F. 1996. *J Immunol* 156:465.)

Cells were plated in 96 well round bottom Costar plates in 100 µl volume for a total of $8 \times 10^3$ while blood cells per well. A total of 80 wells were plated for each blood sample. Sixteen wells on each plate received only media with irradiated spleen cells. On day 7 of culture, supernatants were decanted by inverting the plates and cell pellets suspended by plate agitation. Antigen-positive (Ag-positive) targets were prepared by overnight pulse of P815 cells with 10 ug/ml of the class I-restricted peptide. $1 \times 10^3$ Ag-positive, $^{51}$Cr labeled, P815 targets were added in 100 µl culture media to 50% wells, and $1 \times 10^3$ Ag-negative, $^{51}$Cr labeled, control P815 targets were added to the remaining 50%. Of the 16 wells per plate which contained no effector cells, 8 were designated for spontaneous release and 8 wells for maximum release measurements. Total release was attained by addition of 20 µl of 10% Triton X100. After 4 hour incubation, 50 µl supernatant/well was harvested into Wallac 96 well plates (1450–401), 125 µl scintillant (OptiPhase SuperMix, Wallac, Turku, Finland) added, and plates counted in a Wallac Microbeta 1450.

Calculation of Mean Specific Lysis

Percent lysis for each well was calculated according to the standard formula:

$$\frac{\text{Experimental release} - \text{medium release}}{\text{total release} - \text{medium release}} \times 100$$

where total release was the average cpm of all wells which received targets and triton-X-100, and medium release was the average cpm+SD of all wells which received targets and media only. Mean specific percent lysis per well was calculated according to the formula:

$$\frac{\left(\sum \% \text{ lysis of 40 wells with Ag}^+ \text{ targets}\right) - \left(\sum \% \text{ lysis of 40 wells with control targets}\right)}{40}$$

Data are expressed as mean specific lysis±S.D calculated by averaging the mean specific lysis per well values obtained from each of five mice within a group. Statistical significance was determined using the two tailed Student's t test.

Figure 1:
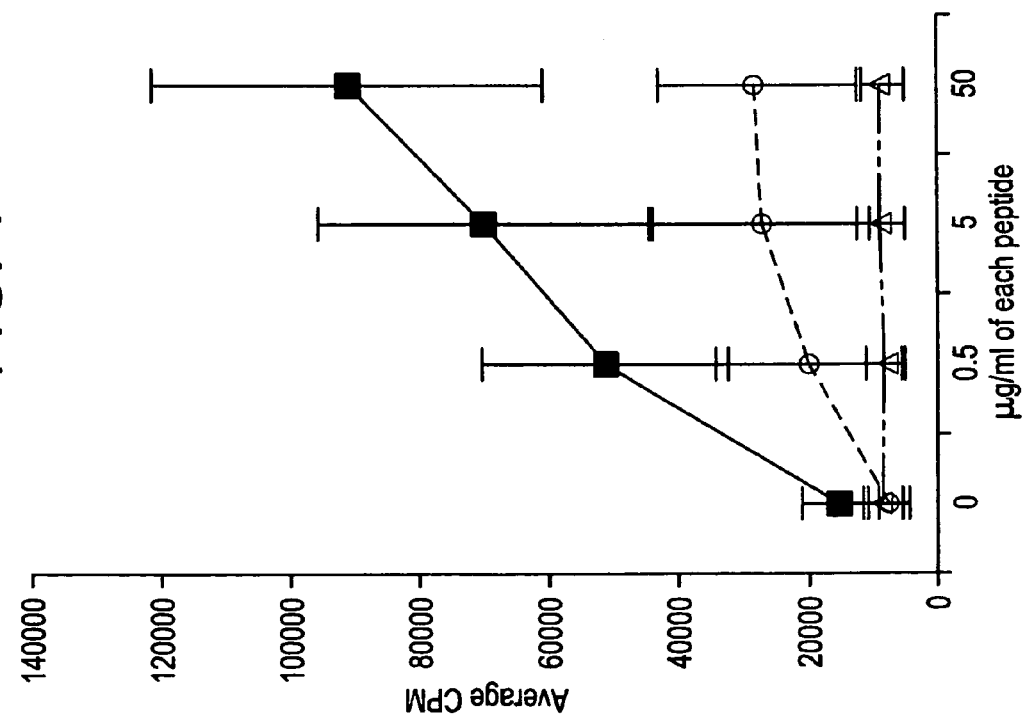
FIG. 1 is a line graph of the antigen specific proliferation of Lymph node cells, as determined by $^3$H-thymidine incorporation, obtained from mice immunized with peptides alone (-O-), treated with B7-2Ig alone (-Δ-), or immunized with peptides and treated with B7-2Ig (-■-). The results indicate an antigen specific proliferative response of cells from mice immunized with Class II-restricted peptides with or without coadministration of B7-2Ig (100 μg).

Results:

B7-2Ig Enhances a Primary CD4+ T Cell Proliferative Response to Immunization with Class II-Restricted Peptides To determine whether B7-2Ig would enhance or suppress the primary T cell response to peptide immunization, mice were immunized with peptides in the presence or absence of B7-2Ig administration. The class II-restricted peptides aa 55–77 and aa 206–229 from NP of A/PR/8/34 influenza virus were delivered subcutaneously as a mixture in IFA. These peptides have been shown to be immunodominant CD4+ Th cell epitopes (Brett, S. J., et al. 1991. *Journal Immunology* 147:1647, Brett, S. J., and J. P. Tite. 1996). Both H-2- and non-H-2-linked genes influence influenza nucleoprotein epitope recognition by CD4+ T cells. *Immunology* 87:42.). B7-2Ig (in 0.1% alum) was administered at a proximal site. In preliminary studies, peptide-specific proliferative responses were measured from lymph node cells on days 3, 5, 7 and 9 post immunization. The kinetics of the response were not affected by administration of B7-2Ig. Optimal proliferative responses were observed from both B7-2Ig and control treated mice at day 7 and 9 post immunization. As shown in FIG. 1, treatment with B7-2Ig at the time of peptide immunization resulted in significantly increased antigen-specific proliferative responses from lymph node cells harvested 9 days post immunization ($p=0.014$, for in vitro restimulation with 50 μg/ml peptide). In FIG. 1 five mice per group were immunized at two subcutaneous sites with an IFA emulsion containing either 100 μg per injection of each of the two class II-restricted peptides or PBS. 100 μg of B7-2IgG2a in 0.1% alum or 0.1% alum alone was administered at sites proximal to the immunization sites. Lymph node cells from mice immunized with peptides alone (-O-), treated with B7-2Ig alone (-Δ-), or immunized with peptides and treated with B7-2Ig (-■-), were harvested 9 days post immunization and restimulated in vitro with the indicated concentration of each of the two peptides used for immunization. Peptide immunized mice which did not receive B7-2Ig received alum as a control. Proliferation was assessed by $^3$H-thymidine incorporation. Data are expressed as the average cpm/well of 5 mice per group±SD. Similar results were obtained when mouse IgG2a mAb was used as a control. Data are from one of three representative experiments. Administration of B7-2Ig in the absence of immunization did not result in proliferative responses demonstrating the antigen dependence of B7-2Ig effects following a primary immunization. These results demonstrate that in vivo administration of B7-2Ig enhances the CD4$^+$ Th cell response to peptide immunization.

B7-2Ig Enhances the Recall Response

To test whether the B7-2Ig dependent enhancement of a primary antigen-specific proliferative response led to an enhanced recall response, mice were immunized with peptides in the presence or absence of B7-2Ig treatment, and boosted forty-six days later without further B7-2Ig administration. Spleen cells were collected 3 days after the second immunization and the peptide-specific proliferative response was measured. As shown in FIG. 2, mice that had received a single B7-2Ig treatment at the time of primary immunization had greater proliferative responses following a second immunization than mice that never received B7-2Ig ($p=0.0006$, for in vitro restimulation with 100 pg/ml peptide). Five mice per group were immunized with peptides alone (-O-), treated with B7-2Ig alone (-Δ-), or immunized with peptides and treated with B7-2Ig (-■-). On day 46 post primary immunization, both groups of peptide immunized mice were re-immunized with peptides in the absence of B7-2Ig coadministration. Non-immunized mice received IFA only. Three days after re-immunization, spleen cells were restimulated in vitro with the indicated concentration of each of the two peptides used for immunization. Proliferation was assessed by $^3$H-thymidine incorporation. Data are expressed as the average cpm/well of 5 mice per group±SD. Data are from one of two replicate experiments. These data indicate that B7-2Ig, when used as an adjuvant for a primary T cell response, enhances the recall response.

B7-2Ig Enhances Both Th1 and Th2 Dependent Primary Cytokine Responses

To determine whether B7-2Ig as immune adjuvant differentially promoted development of Th1 or Th2 responses, peptide-specific cytokine responses following primary immunization were analyzed from lymph node cells of immunized mice at 3,5,7 and 9 days post immunization. Just as with proliferative responses, optimal cytokine responses were observed at day 9. As shown in Table I, administration of B7-2Ig at the time of immunization with peptides resulted in significantly increased levels of production of the Th1 associated cytokine IFN-γ ($p=0.017$), and the Th2 associated cytokines IL-5 ($p=0.011$), and IL-13 ($p=0.002$). Antigen specific cytokine production was not observed in cultures from unimmunized mice treated with B7-2Ig. These results indicate that B7-2Ig enhances a primary T cell response of both Th1 and Th2 phenotypes.

B7-2Ig Enhances CTL Response to Class I-Restricted Peptide.

Interaction of membrane bound B7 with CD28 has been shown to allow induction of in vitro CTL responses in the absence of CD4+ cells (Harding, F. A. et al. 1993, *J Exp Med* 177:1791). To test the effect of B7-2Ig on the primary CTL response, mice were immunized with the immunodominant class I-restricted peptide in IFA with or without concomitant B7-2Ig administration. Peptide specific CTL responses were measured from unfractionated peripheral blood cells using the small blood sample, CTL assay as described in Materials and Methods. This assay makes possible the analysis of large numbers of mice within a single experiment, assessment of the statistical significance of differences between groups, repeated CTL assays from individual mice during the course of an immune response, and investigation of correlation between CTL responses and in vivo results.

Figure 3:
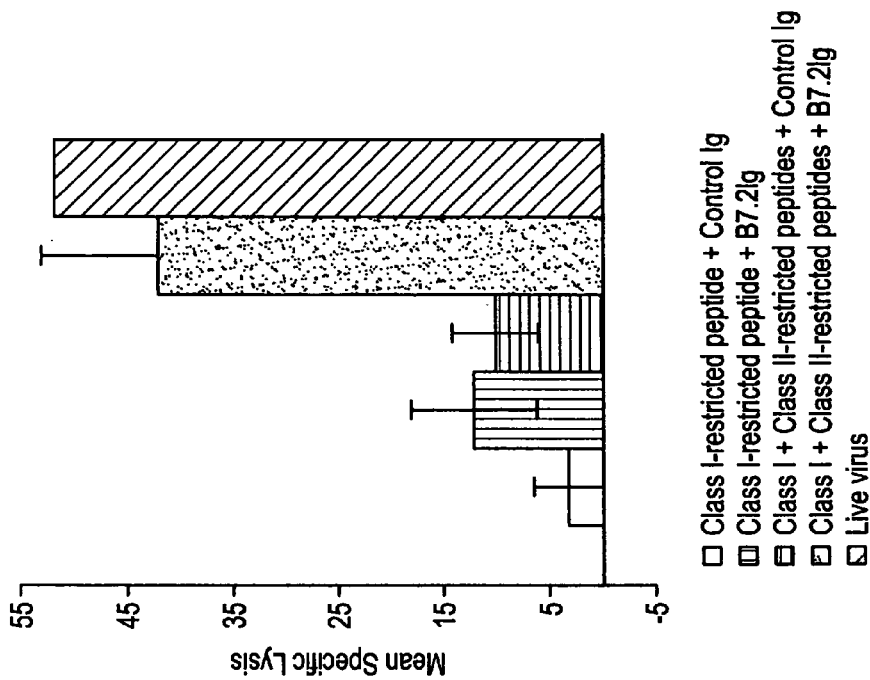
FIG. 3 is a bar graph of the peptide specific CTL response of unfractionated peripheral blood cells, shown as mean specific lysis, from mice immunized with immunodominant Class I-restricted peptide in IFA, with or without concomitant B7-2Ig administration. The results indicate that B7-2Ig coadministration enhances the CTL response to immunization with Class I-restricted peptide.

Data are expressed as a single value (mean specific lysis) per mouse (FIG. 3). Peptide (100 μg/mouse) was given in IFA. B7-2Ig (100 μg in 0.1% alum/mouse) was coadministered subcutaneously. CTL were measured from unfractionated blood collected three weeks after immunization. Data are expressed as mean specific lysis±SD. Value for the live virus immunized group is from a single pool of 2 mice, and the average mean specific lysis of this group was 52±12 obtained from 18 mice tested in 9 separate experiments. There were five mice per group in all other groups. The data shown is from one of three replicate experiments. Responses to class I-restricted peptide in IFA were not significantly above background. This finding is consistent with those of Fayolle et al. 1991 *Journal Immunology* 147:406) who showed that in the absence of T cell help, the CTL response to class I-restricted peptide in IFA was close to background levels. When B7-2Ig was administered at the time of immunization with class I-restricted peptide in IFA, a small but statistically significant ($p=0.013$) increase in the response was observed (FIG. 3). However, the magnitude of the peptide specific CTL response of mice immunized with peptide and coadministered B7-2Ig was small in comparison to the peptide specific response of mice immunized with live virus. Therefore coadministration of a dose of 100 μg B7-2Ig does not elevate the response to immunization with class I-restricted peptides to the maximal level achieved with the effective live virus immunization method.

Optimal B7-2Ig Enhancement of CTL Response Requires T Cell Help.

Figure 4:
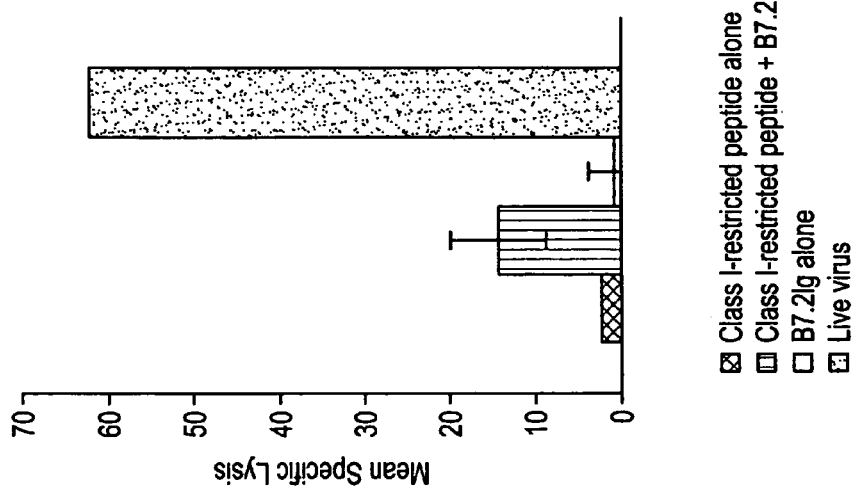
FIG. 4 is a bar graph of the peptide specific CTL response of unfractionated peripheral blood cells, shown as mean specific lysis, from mice immunized with an IFA emulsion containing either Class I-restricted peptide alone or a mixture of Class I-restricted peptide and two Class II-restricted peptides, described for FIGS. 1 and 2 above. The result represent the CTL response of mice immunized with Class I-restricted peptide in the presence or absence of Class II-restricted peptide and B7-2 Ig treatment.

Since optimal CTL responses depend on Th cells (Fayolle, C. et al. 1991, *Journal Immunology* 147:4069; Keene, J. A. et al. 1982, *J Exp Med* 155:768; von Herrath, M. G. et al. 1996 *J Virol* 70:1072 and Ossendorp, F. et al. 1998, *Journal Experimental Medicine* 187:693) the effect of B7-2Ig on CTL responses was tested under conditions where mice were co-immunized with peptides known to elicit Th cell responses. Mice were immunized with an IFA emulsion containing either the class I-restricted peptide alone or a mixture of the class I-restricted peptide and the two class II-restricted peptides described for FIGS. 1 and 2 and Table 1 above. CTL responses were measured from unfractionated peripheral blood cells (FIG. 4). Peptide immunization was done as a single emulsion in IFA. Mice were immunized and treated as indicated. Three weeks later, CTL responses were measured from peripheral blood. Data are expressed as mean specific lysis±SD. The value for the live virus immunized group is from a single pool of 2 mice, and the average mean specific lysis of this group was 52±12 obtained from 18 mice tested in 9 experiments. There were five mice per group in all other groups. Mean specific lysis of the group which received Class II-restricted peptides in IFA and control Ig in alum has been subtracted from groups shown which received control Ig. Mean specific lysis of the group which received class II-restricted peptides in IFA and B7-2Ig in alum has been subtracted from groups shown which received B7-2Ig. The data shown are from one of four replicate experiments.

Mean specific lysis of cells from mice immunized with the mixture of class I and class II-restricted peptides was significantly higher than of cells from mice immunized with class I-restricted peptide alone (p=0.046 in experiment shown and 0.004 in a replicate experiment). Immunization with the mixture of class I-restricted and class II-restricted peptides and treatment with 100 µg B7-2Ig resulted in a mean specific lysis significantly greater than that from peptide immunized mice that did not receive B7-2Ig (p=0.003, p=0.0001, p=0.045 and p=0.0012 in four replicate experiments). This response was not increased when the dose of B7-2Ig was increased two fold to 200 µg/mouse, indicating that the 100 µg dose induced the maximum B7-2Ig dependent enhancement.

The combination of immunization with the mixture of peptides together with B7-2Ig treatment resulted in peptide-specific CTL responses similar in magnitude to those elicited following immunization with live virus. A mean specific lysis value of 52±12 was obtained when the values obtained from 18 live virus immunized mice in 9 separate experiments were averaged, demonstrating the reproducibility of the small peripheral blood sample CTL assay and the validity of the conclusion that peptide immunization in the presence of T cell help and B7-2Ig elicits responses comparable to those elicited by the efficient live virus method of immunization. The CTL response detected from peripheral blood cells peaked at 2 to 3 weeks and waned in the fifth week in both mice immunized with live virus and mice immunized with peptides and treated with B7-2Ig, again indicating similarity of the responses. As discussed below, however, mice immunized with the peptide mixture and treated with B7-2Ig were not protected from lethal virus challenge.

The data in FIGS. 3 and 4 were generated with B7-2Ig formulated in 0.1% alum, which is itself a clinically approved immune adjuvant (Aprile, M. A. et al. 1966, *Can J Public Health* 57:343). Administration of alum alone or control Ig in alum did not affect the anti-peptide response, and formulation in alum was not required for B7-2Ig dependent immune enhancement. Formulation in alum does, however, potentiate the effects of B7-2Ig. When the effect of B7-2Ig in alum were directly compared to the effects of B7-2Ig in PBS, greater enhancement of the CTL response was observed when B7-2Ig was administered in alum (mean specific lysis 72±13 with alum compared to 38±12 without, p=0.007).

Optimal antigen-specific activation and regulation of T cells requires the delivery of a costimulatory signal from B7 molecules on the surface of the APC to CD28 and CTLA-4 on the surface of the T cell (Boussiotis, V. A., et al. 1996, *Immunol Rev* 153:5; Lenschow, D. J. et al. 1996, *Annual Review Immunology* 14:233; Green, J. M. et al. 1994. *Immunity* 1:501; Tivol, E. A. et al. 1995, *Immunity* 3:541 and Waterhouse, P., 1995, *Science* 270:985). Work in a wide variety of mouse models has shown that immune responses can be enhanced by increased cell surface expression of B7. In these studies, increases in B7 expression have been induced by tumor cell transduction (Baskar, S. et al. 1993, *Proc Natl Acad Sci USA* 90:5687; Cavallo, F. et al. 1995, *Eur J Immunol* 25:1154; Coughlin, C. M. et al. 1995, *Cancer Research* 55:4980; Chen, L., et al. 1992, *Cell* 71:1093; Chen, L. et al. 1994, *Journal of Experimental Medicine* 179:523; Gajewski, T. F. et al. 1996, *J Immunol* 8:2909; Yang, G. et al. 1995, *Journal of Immunology* 154:279 and Dunussi-Joannopoulos K, et al. 1996, *Blood* 87:2938) cDNA injection (Kim, J. J. et al. 1997, *Nat Biotechnol* 15:641; Kim, J. J. et al. 1998, *Vaccine Nov*; 16:1828 and Horspool, J. H. et al. 1998, *J Immunol* 160:2706), or infection with viral vector (Chamberlain, R. S. et al. 1996, *Cancer Res* 56:2832; Emtage, P. C. et al. 1998, *J Immunol* 160:2531; Hodge, J. W. et al. 1994, *Cancer Res* 54:5552 and Putzer, B. M. et al. 1997, *Proc Natl Acad Sci USA* 94:10889). Using a different strategy for increasing B7 levels in vivo, a soluble protein form of B7-2, B7-2Ig has been developed, consisting of the Fc of mouse IgG2a fused with an extracellular portion of B7-2 attached to each Ig chain. In vivo administration of B7-2Ig enhances antigen specific Th cell and CTL responses. Thus in vivo administration of B7-2Ig presents a simple alternative to ex vivo B7 transduction of tumor cells or the use of viral or DNA vectors for optimizing B7-2 mediated costimulation.

Because the outcome of infectious and autoimmune diseases can be greatly affected by the pattern of cytokines produced by responding Th cells, there has been interest in determining whether the B7 pathway could to be utilized to skew towards either Th1 or Th2 type cytokine responses (Kuchroo, V. K. et al. 1995, *Cell* 80:10; Lenschow, D. J. et al. 1995, *J Exp Med* 181:1145; Corry, D. B. et al. 1994, *J Immunol* 153:4142; Freeman, G. J. et al. 1995, *Immunity* 2:523; Schweitzer, A. N. et al. 1997, *J Immunol* 2 158:713; Rulifson, I. C. et al. 1997, *J Immunol* 158:658 and McAdam, A. J. et al. 1998 *Immunol Rev* 165:231). A number of experimental systems indicate that Th2 differentiation is more dependent on B7 costimulation than is Th1 differentiation (Lenschow, D. J. et al. 1995, *J Exp Med* 181.1145; Corry, D. B., et al. 1994, *J Immunol* 153:4142; Freeman, G. J. et al. 1995, *Immunity* 2:523 and Rulifson, I. C., A. et al. 1997, *J Immunol* 158:658). Anti-B7 mAb have been successfully used to manipulate T cell differentiation in vivo. Blockade of B7-1 with mAb has been reported to favor Th2 differentiation, whereas blockade of B7-2 favors Th1 differentiation (Kuchroo, V. K. et al. 1995, *Cell* 80: Mar 10(5); Lenschow, D. J. et al. 1995, *J. Exp Med* 181:1145; Corry, D. B. et al. 1994, *J Immunol* 153:4142; Freeman, G. J. et al.

1995, Immunity 2:523 and Rulifson, I. C. et al. 1997, J Immunol 158:658). In contrast, using APC from B7 knockout mice, Schweitzer et al. found that neither B7-1 nor B7-2 appear to selectively regulate Th1 or Th2 differentiation in vitro (Schweitzer, A. N. et al. 1997, J Immunol 2 158:713). The data in this example show that in vivo administration of B7-2Ig enhances antigen specific cytokine responses of both the Th1 and Th2 type. Therefore the therapeutic potential B7-2Ig is likely to be greatest in situations where elevation, not skewing, of the response is the goal.

To test the effects of B7-2Ig on CTL responses, the peptide specific CTL response elicited with a peptide from NP of influenza virus A/PR/8/34 to the response elicited to the same peptide from mice immunized with live virus was compared. B7 2Ig treatment induced a small but significant enhancement of the response to class I-restricted peptide in IFA. These data are consistent with data demonstrating that in the absence of exogenous help, tumor cells transfected with B7 are sufficient for the generation of an in vitro CTL response (Harding, F. A. et al. 1993, J Exp Med 177:1791).

The B7-2Ig enhanced response, however, was significantly lower than the CTL response to the same peptide of mice immunized with live virus. These data show that the mice are capable of a much greater anti peptide response than that which is elicited by class I-restricted peptide immunization and B7-2Ig coadministration.

In an attempt to further enhance the response to the class I-restricted peptide the effects of adding Th cell, class II-restricted, peptide antigens to the IFA emulsion containing the class I-restricted CTL peptide antigen were investigated. It has been previously reported that optimal CTL responses depend on Th cells (Fayolle, C. et al. 1991, Journal Immunology 147:4069; Keene, J. A. et al. 1982, J Exp Med 155:768; von Herrath, M. G. 1996, J Virol 70:1072 and Ossendorp, F. et al. 1998 Journal Experimental Medicine 187:693). CTL responses were significantly elevated in mice immunized with both class I and class II-restricted peptides. These data indicate that help for a CTL response against a peptide antigen can be provided by co-immunization with Th cell antigens. Covalent links between CTL and Th peptide epitopes are not required, suggesting that any immunogenic protein can be used as a co-immunogen to provide help for CTL responses. This conclusion is further supported by our finding that addition of KLH to an IFA emulsion containing class I-restricted peptide results in significant enhancement of the peptide specific CTL response.

Although enhanced, the peptide specific CTL response of mice immunized with class I and class II-restricted peptides was less than that of mice immunized with live virus. Addition of B7-2Ig to the protocol increased the CTL response of mice immunized with the mixture of peptides to the level of mice immunized with live virus. Responses of these two groups were comparable, but the former group was not protected from lethal virus challenge. This result is consistent with those of Lawson et al. (Lawson, C. M. et al. 1994, Journal Virology 68:3505), who elicited a vigorous CTL response against the same peptide used in this study by administration of recombinant vaccinia virus expressing the peptide. As in the present, a vigorous CTL response to this peptide alone was not sufficient to confer protective immunity in BALB/c mice.

Although not required for the immune enhancing effects of B7-2Ig, formulation in alum results in greater enhancement than formulation in PBS. Administration of control Ig in alum does not affect responses, indicating that alum alone does not enhance the response.

Infection with live virus is the natural and effective pathway for activation of class I-restricted responses (Zinkernagel, R. M. et al. 1979, Adv Immunol 27:51). Therefore, the data presented here showing that comparable anti-peptide responses were obtained from mice immunized with live virus and B7-2Ig treated mice immunized with a mixed emulsion of class I and class II-restricted peptides establishes the effectiveness of the latter immunization protocol. Currently there is much interest in elicitation of CTL responses to class I-restricted peptides. Demonstrations in recent years that human CTL can, like mouse CTL, recognize class I-restricted, tumor associated peptides has suggested that CTL responses directed against these peptides may prove effective against human tumors (van der Bruggen, P. et al. 1991, Science 254:1643; Wolfel, T. et al. 1993, Int. J. Cancer 55:237; Maeurer, M. J. 1996, Melanoma Res 6:11; Cormier, J. N. et al. 1997, Cancer J Sci Am 3:37; Apostolopoulos, V. et al. 1997, J. Immunology 159:5211; Rosenberg, S. A. 1998, Nature Medicine 4:321 and Nestle, F. O. et al. 1998, Nature Medicine 4:328). This possibility has spurred an intense effort to devise immunization protocols which optimize responses to class I-restricted peptide vaccines. Success has been reported with a wide variety of strategies including minigene insertion into recombinant virus and bacteria, peptide oligomerization, lipid modification, cDNA immunization, use of toxins and cytokines as adjuvants, and antigen pulsed dendritic cells (Allsopp, C. E. et al. 1996, European Journal of Immunology 26:1951; Rotzschke, O. et al. 1997, Proc Natl Acad Sci USA 94:14642; Alving, C. A. et al. 1995, Immunological Reviews 145:1; Ciernik, I. F. et al. 1996, J Immunol 156:2369; Porgador, A. et al., 1997, Journal of Immunology 158:834; Noguchi, Y. et al. 1995, Proceedings of the National Academy of Science; USA 92:2219 and Takahashi, H. et al. 1992, International Immunology 5:849). The advantage of the method reported here is that it is uniformly applicable to any peptide without necessity of further modification and is effective for both class I and class I-restricted responses.

The co-administration of B7-2Ig with peptide immunization elevates a relatively poor class I-restricted peptide response to a level comparable to that resulting from live virus immunization suggests that a soluble form of B7-2 protein could also enhance responses to other poor immunogens. These findings show that soluble protein forms of B7-2 may enhance antigen-specific immune responses in cancer or infectious disease therapy where the immune system responds ineffectively.

TABLE 1

B7-2Ig Dependent Enhancement of Th Cytokine Responses[a]
Expression of Cytokine On In Vitro Restimulation

| In Vivo Treatment | IFNγ (pg/ml ± SD) | IL-5 (pg/ml ± SD) | IL-13 (pg/ml ± SD) |
|---|---|---|---|
| Peptide Immunization | b.d[b] | 54 ± 44 | 136 ± 125 |
| Peptide Immuniz. Plus B7-2Ig | 1720 ± 986 | 2479 ± 1104 | 5365 ± 1795 |
| IFA Plus B7-2Ig | b.d[b] | b.d[b] | b.d[b] |

[a]Five mice per group were immunized at two subcutaneous sites with an IFA emulsion containing either 100 μg per injection of each of the two class II-restricted peptides or PBS. 100 μg of B7-2IgG2a in 0.1% alum or 0.1% alum alone was administered at sites proximal to the immunization sites. Nine days later, lymph node cells were harvested and restimulated in culture for three days with 5 μg/ml of each peptide.Values for each mouse were obtained by averaging results from triplicate wells. Data are expressed as the average concentration of cytokine of mice within a group ±SD. Results are similar to those obtained when a control mouse IgG2a mAB was used as control. Data shown are from one of three replicate experiments.
[b]Below the limits of detection of assay.

Example 2

B7-IgG Fusion Proteins Enhance Anti-Tumor Immune Responses and Induce Regression of Established Tumors Fusion proteins between an extracellular region of either B7-1 or B7-2 and IgG.2a have been evaluated for their ability to enhance anti-tumor responses in four different murine tumor models, including the poorly immunogenic melanoma B 16/F10. A single vaccination with irradiated tumor cells when mixed with B7-1 or B7-2-IgG protected mice against a live tumor challenge. More significantly, 7-day established tumors regressed after vaccination with irradiated tumor cells mixed with B7-IgG. Even therapeutic administration of B7-IgG alone achieved similar decreases in tumor burden. Animals that had rejected an established tumor were resistant to a rechallenge, strongly suggesting that the anti-tumor effect of B7-IgG is mediated by tumor-specific immune mechanisms. In addition, a single vaccination with irradiated tumor cells mixed with B7-1 or B7-2-IgG generated CD8 responses against a tumor-associated antigen. Thus, B7-IgG exhibits potent adjuvant activity in combination with exogenously delivered and endogenous antigens. These findings suggest clinical value for B7-Ig to enhance anti-tumor and anti-viral responses.

Materials and Methods Used in Example 2

The expression plasmids for the murine B7-1-IgGIgG and B7-2-IgG2a fusion proteins were constructed by joining the DNA encoding the signal and extracellular domains of murine B7-1 or B7-2 to the DNA encoding the hinge-CH2—CH3 domains derived from a murine IgG2a antibody. The cysteine residues within the antibody hinge region remained conserved such that the mB7-1-IgGIgG2a or mB7-2-IgG2a produced is dimeric and bivalent. Fusion proteins were generated in which the IgG2a region is mutated in order to prevent binding by high affinity Fc receptors and complement activation (designated B7-IgG2mut). The following amino acid residues in the CH2 domain were replaced by alanine: leucine at position #235, glutamic acid at #318, lysine at #320, and lysine at #322. For production of B7-IgG protein, the plasmids were expressed in CHO cell lines and the proteins were isolated.

P815 is a mastocytoma derived tumor cell line that grows as a solid tumor after intradermal (i.d.) injection of $5 \times 10^4$ cells into DBA/2 mice (Jackson Laboratories). The clone used in these experiments metastasizes spontaneously after i.d. injection and leads to the death of the mice after 25-35 days. MethA, a tumor cell line derived from a sarcoma in Balb/C mice, grows as solid tumor after i.d. injection of $5 \times 10^5$ cells (Balb/C mice from Taconic). B16/F10, a non-immunogenic tumor line derived from a melanoma in C57BL/6 mice (Taconic), grows as a solid tumor after i.d. injection of $1 \times 10^5$ cells and causes death due to metastases after 25-35 days. The bladder carcinoma MB49 is also derived from C57BL/6 mice and $1 \times 10^5$ cells were injected i.d. to establish solid tumors after 5-7 days in 100% of mice.

In Vitro Costimulation Assay $2 \times 10^5$ naive murine splenocytes were plated in triplicate in 96-well plates coated with low concentrations of anti-CD3 mAb (0–500 ng-ml of –2C11, Pharmingen). To provide the necessary signals for costimulation, the plates were either co-coated with anti-CD28 mAb (0–1 µg/ml) as positive control or with B7-1-IgG or B7-2-IgG (0–9 µg/ml). B7-IgG was also added in soluble form or cross-linked by a secondary anti-mouse IgG2a Ab. The splenocytes were stimulated for 72 hours. An aliquot of supernatant was removed for IFN-γ analysis and the cells were pulsed for 8 h with H³-thymidine. IFN-γ analysis was performed in a standard ELISA with the capture Ab R46A4 and biotinylated XGM1.2 as detection Ab.

Vaccination Protocols:

In a prophylactic tumor vaccine model, mice were vaccinated on day 0 at the same time that they were challenged with tumor cells. Mice were immunized with irradiated tumor cells ($1 \times 10^7$ cells) in PBS, mixed with 75–100 µg of mB7-1-IgG, B7-2-IgG, murine IgG, or nothing. The injection was given intra-footpad (i.fp.) in both hindlegs. Injection of B7-IgG was repeated once on day 3 or 5. On day 7, animals were challenged with a defined dose of live tumor cells by i.d. injection of 50 µl in the right flank. Growth of the primary tumor and survival of animals was monitored over 40–60 days.

In a therapeutic tumor vaccine model, a primary tumor was established by i.d. inoculation with a defined number of tumor cells. On day 5–7 (when tumors were clearly palpable), mice were vaccinated i.fp. with $1 \times 10^7$ irradiated tumor cells mixed with 100 µg of B7-1-IgG, B7-2-IgG, or nothing. 100 µg B7-IgG was again injected i.fp. three days later. This vaccination regimen was repeated for two or three weeks. Growth of primary tumor and survival of mice was monitored from day 7 to day 40–70.

In therapy models, tumor-bearing mice B7-IgG were treated with fusion protein alone. 50–100 µg of B7-1-IgG or B7-2-IgG alone was injected i.fp. twice a week for three weeks. Tumor growth and survival was monitored for 40 days.

Detection of P1A-Specific CTL Responses:

Spleens were collected from DBA/2 mice 10-14 days after a single immunization with irradiated P815 cells mixed with or without B7-1-IgG or B7-2IgG. After lysis of erythrocytes $20 \times 10^6$ splenocytes were restimulated in T25 flasks with 0.1 ng/ml P1A peptide and 5 U/ml IL-2 (Pharmingen) for 6 days. Then, a standard 5 h $Cr^{51}$-release assay was performed with A20 cells as targets pulsed with 10 µg/ml of P1A peptide or unpulsed with peptide. The percent of P1A-peptide specific lysis is expressed as the difference between the percent lysis of peptide-pulsed targets and the percent lysis of unpulsed targets.

Results:

Immobilized or Cross-Linked B7-IgG Provides Costimulatory Signal for Suboptimally Stimulated Murine Splenocytes In Vitro.

Figure 5A:
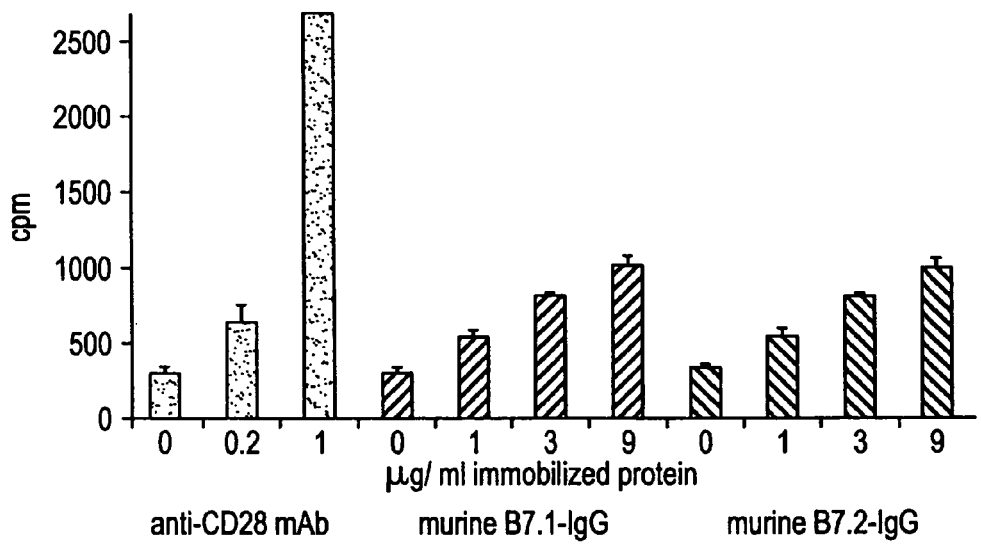
FIGS. 5A, B and C are bar graphs of the response of murine splenocytes stimulated in vitro by culturing with plate-bound anti-CD3 mAb in combination with the indicated plate bound protein(s).
Figure 5B:
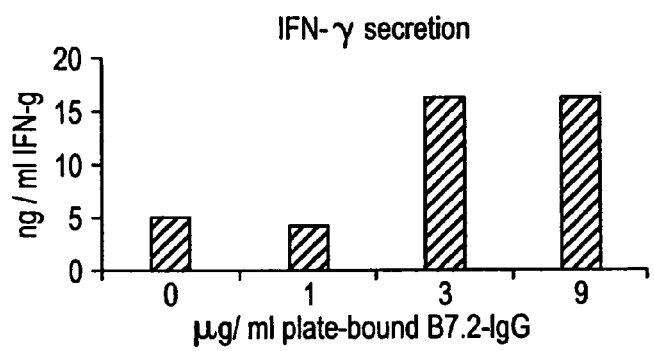
FIG. 5B is a bar graph of IFN-γ secretion.
Figure 5C:
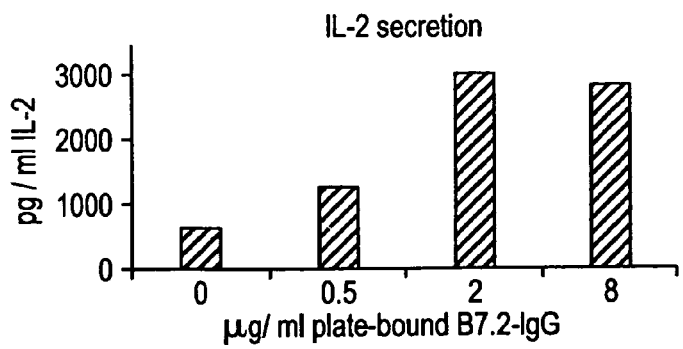
FIG. 5C is a bar graph of IL-2 secretion. The results indicate that B7-IgG provides a co-stimulatory signal for in vitro proliferation and lymphokine secretion in splenocytes.
Figure 7A:
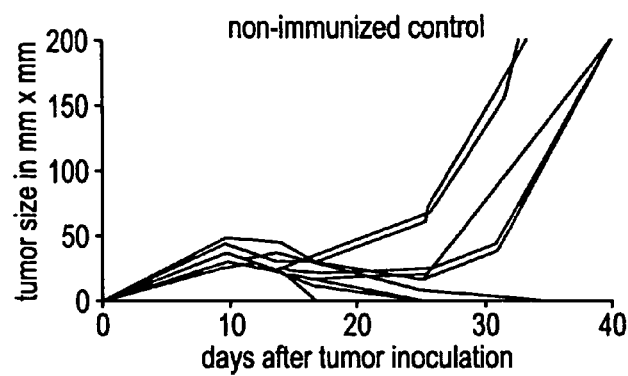
FIGS. 7A–H is a series of line graphs indicating tumor size in DBA/2 mice with established P815 tumors which were inoculated with either PBS as control (A, E), or with irradiated P815 tumor cells alone (B) or mixed with irrelevant mouse IgG2a Ab (F), or with irradiated P815 cells mixed with B7-1 (C)- or B7-2-IgG (G); and also survival times of the different treatment groups (D and H). The results indicate that therapeutic vaccination of mice with irradiated P815 tumor cells mixed with B7-1- or B7-2-IgG induces tumor regression and prolonged survival.
Figure 7B:
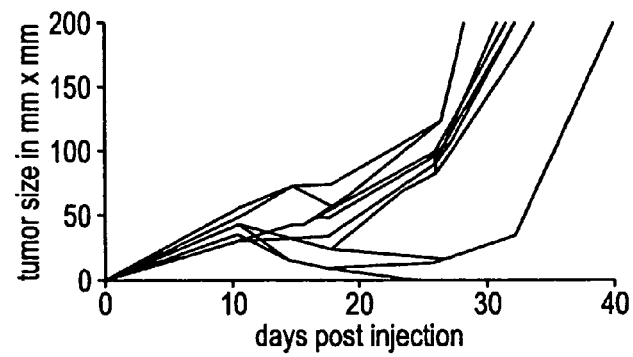
Figure 7C:
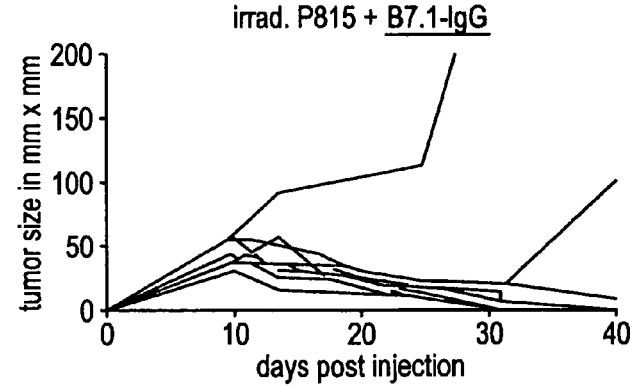
Figure 7D:
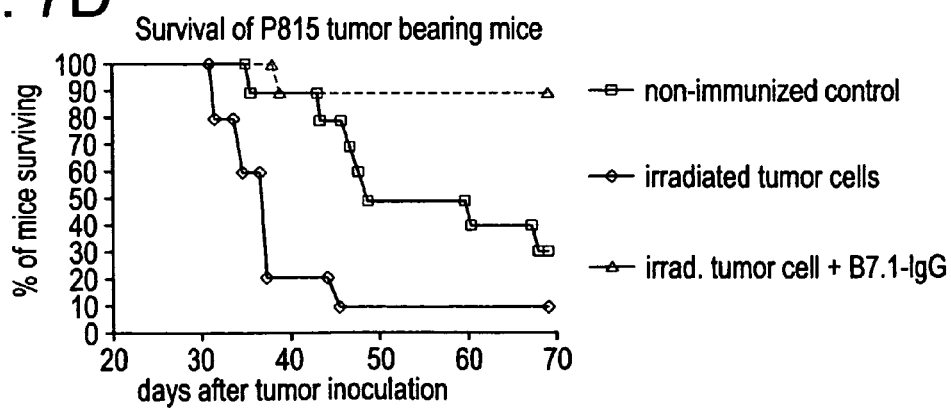
Figure 7E:
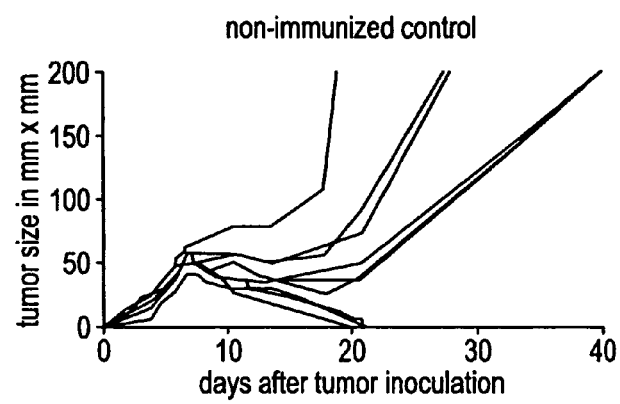
Figure 7F:
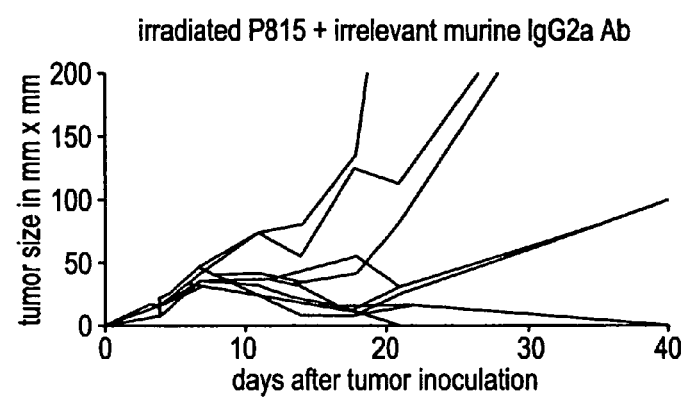
Figure 7G:
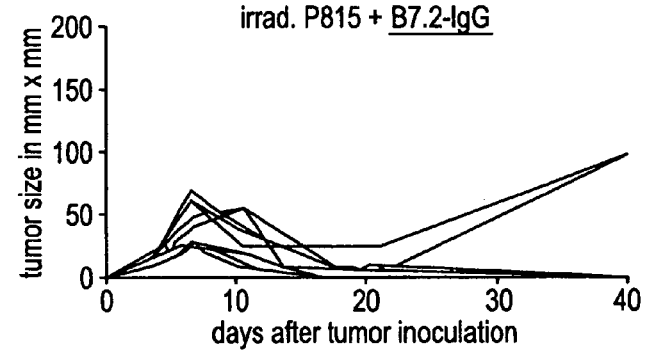
Figure 7H:
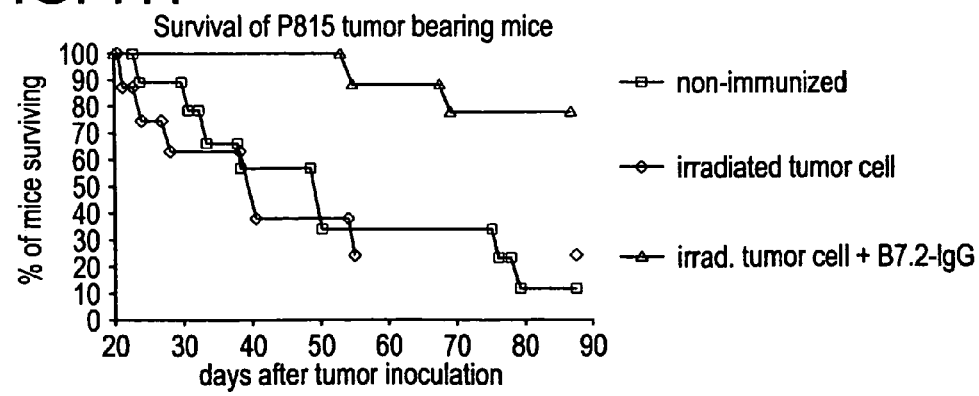
Figure 8A:
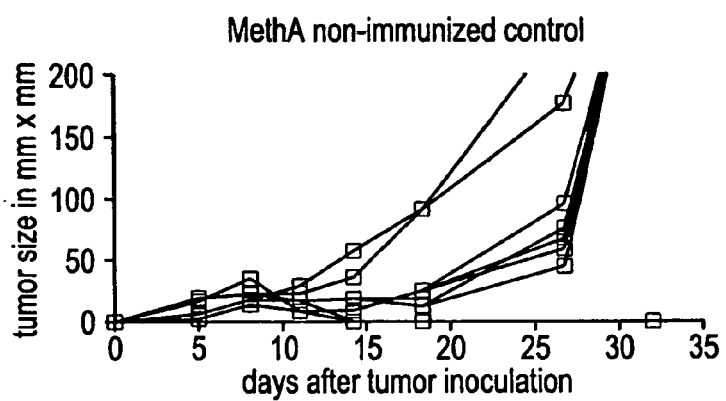
FIGS. 8 A–H is a series of line graphs indicating tumor size in Balb/c mice with established MethA sarcomas, inoculated with PBS (A), irradiated tumor cells alone (B, E), or mixed with 25 μg (C, D) or 100 μg (F, G) B7-1-IgG or B7-2-IgG, respectively, and given an additional injection of PBS, or B7-1-IgG, B7-2-IgG, respectively, 34 days later; and also survival times of the different treatment groups (H). The results indicate that immunization of mice with B7-IgG as an adjuvant for a therapeutic tumor cell vaccine is effective in several different mouse tumor models.
Figure 8B:
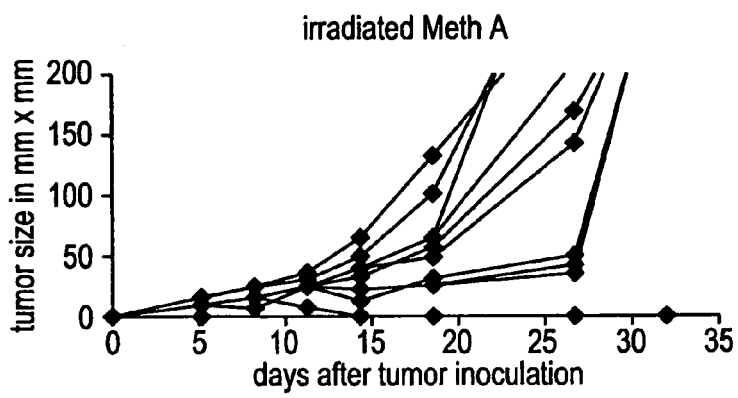
Figure 8C:
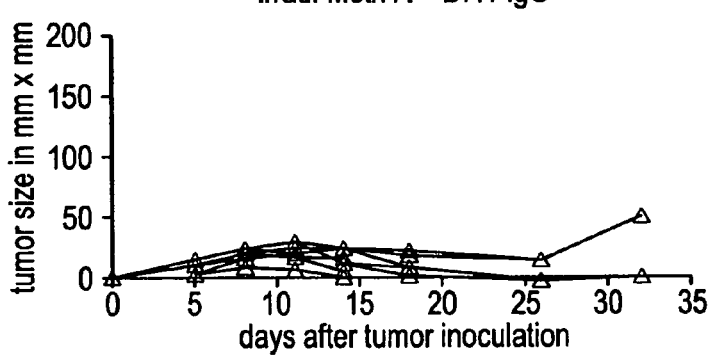
Figure 8D:
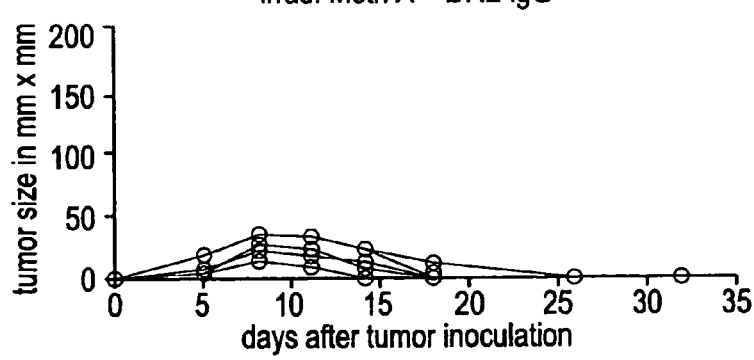
Figure 8E:
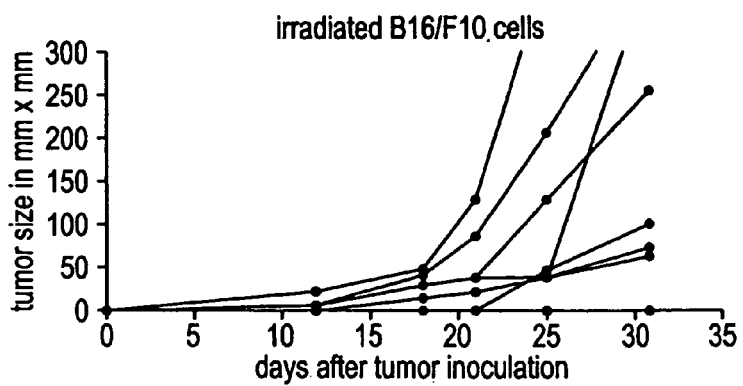
Figure 8F:
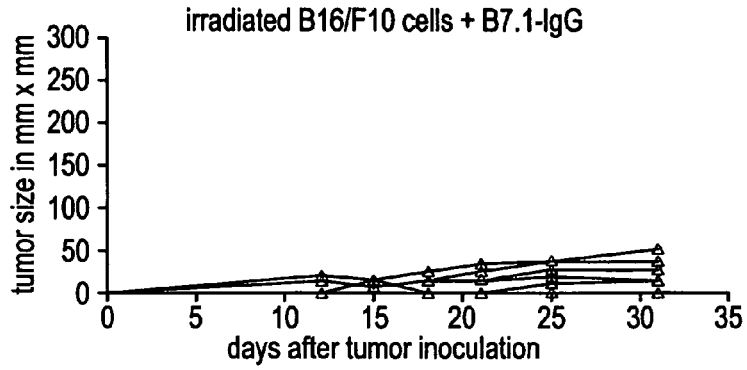
Figure 8G:
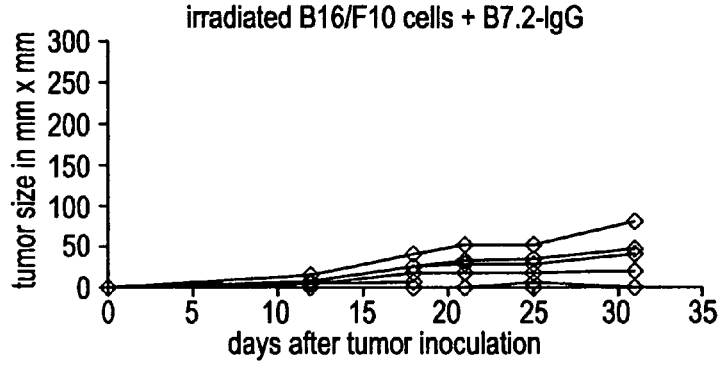
Figure 8H:
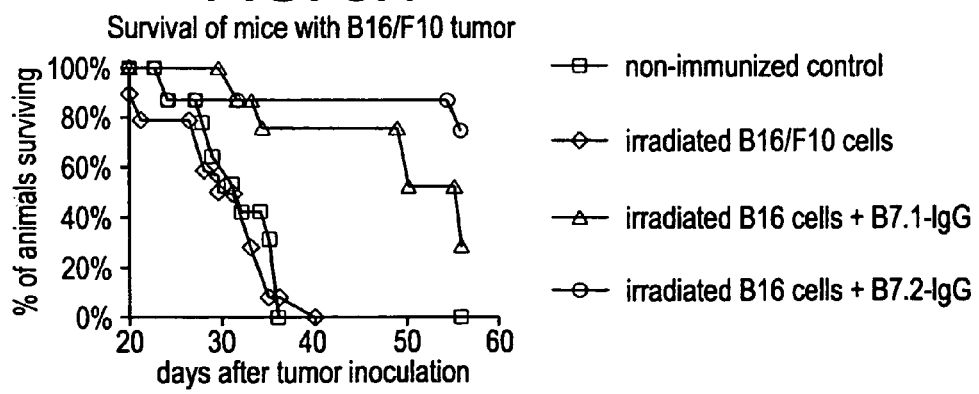
Figure 9A:
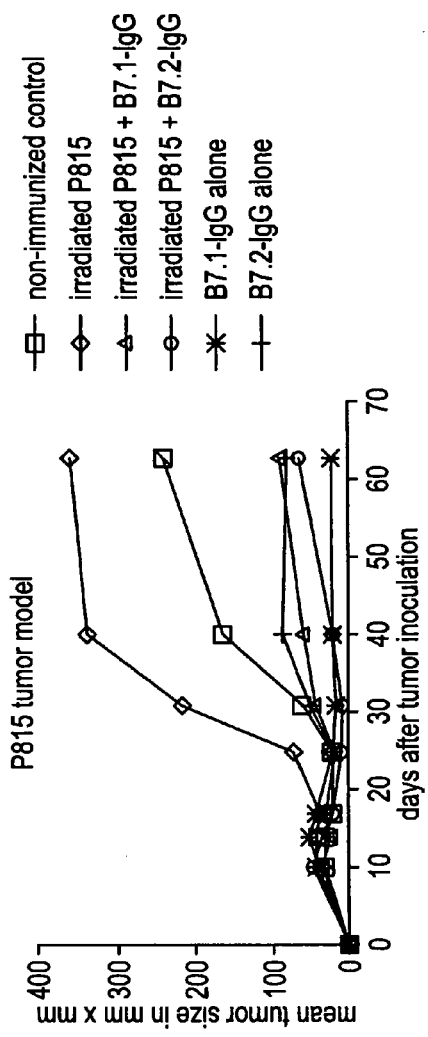
FIGS. 9 A–D is a series of line graphs indicating tumor size in various mouse tumor models which were treated with PBS (□), irradiated tumor cells alone (◊), irradiated tumor cells mixed with B7-1-IgG (Δ), or B7-2-IgG (O), or with B7-1-IgG (*) or B7-2-IgG alone (+). (A) P815 tumor model, (B) MethA tumor model, (C) MB49 tumor model, and (D) B16/F10 tumor model. Results indicate that the anti-tumor effect of therapeutic administration of B7-IgG alone in mice is comparable to its effect as vaccine adjuvant.
Figure 9B:
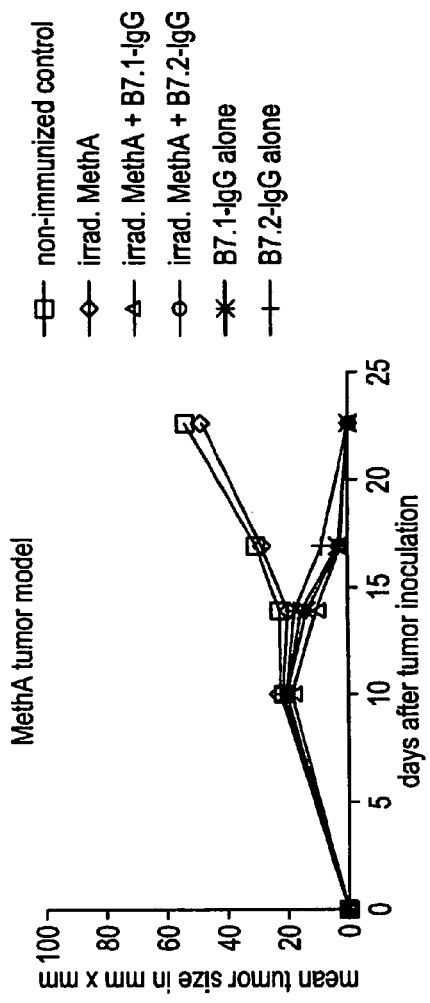
Figure 9C:
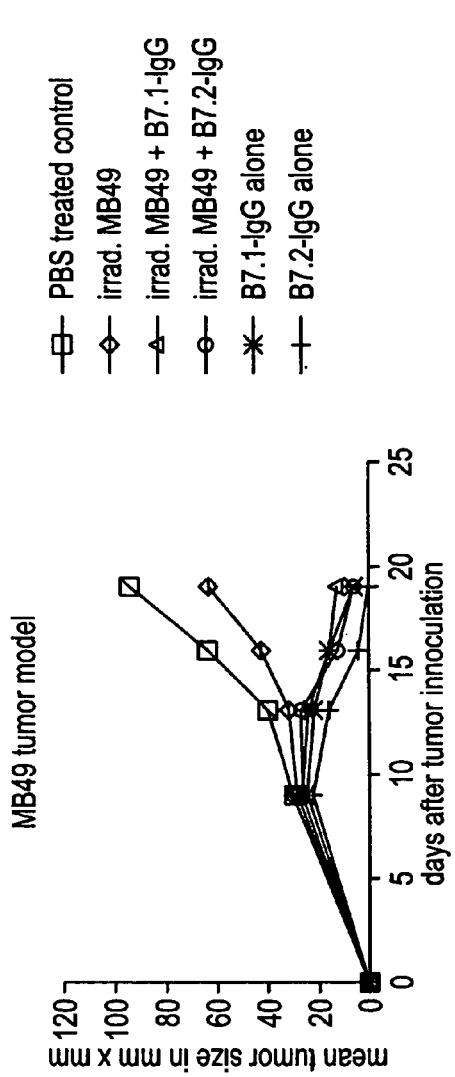
Figure 9D:
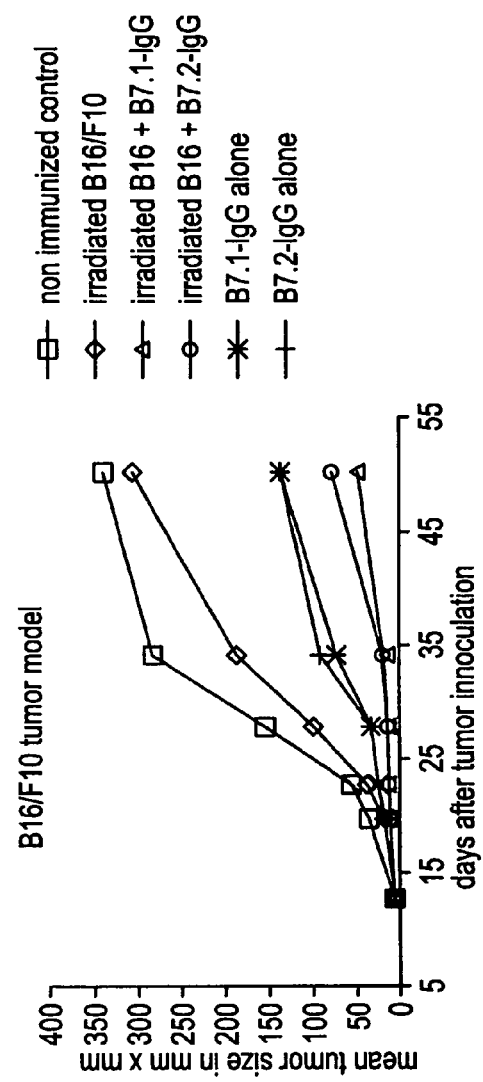
Figure 10A:
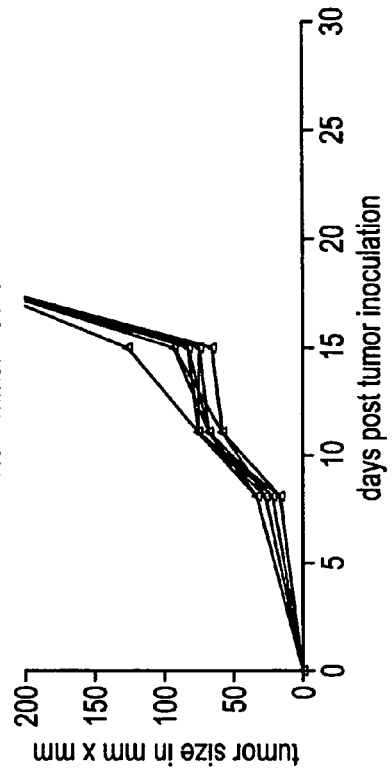
FIGS. 10 A–D is a series of line graphs indicating tumor size in Balb/c mice (SCID mice or wild-type) which had solid tumors and were non-immunized control SCID mice (A), SCID mice which received treatment with B7.2-IgG (B), SCID mice which were vaccinated with irradiated MethA and B7.2 (C), and wild-type mice treated with B7.2-IgG (D). The results indicate that T or B cells are required for B7-IgG-mediated anti-tumor activity.
Figure 10B:
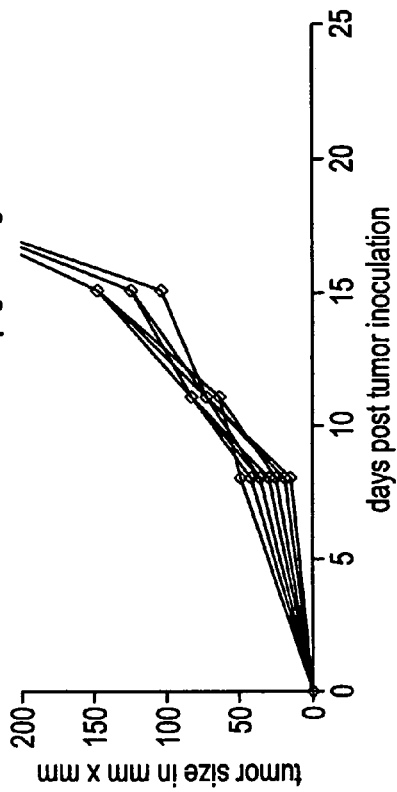
Figure 10C:
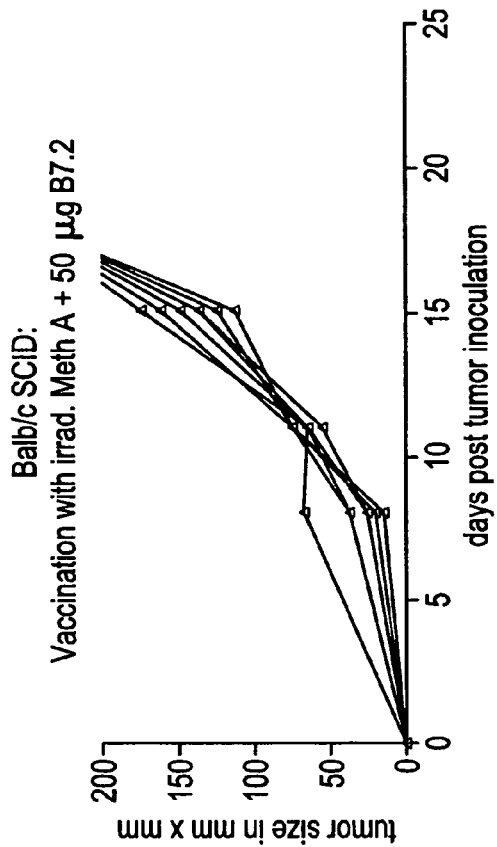
Figure 10D:
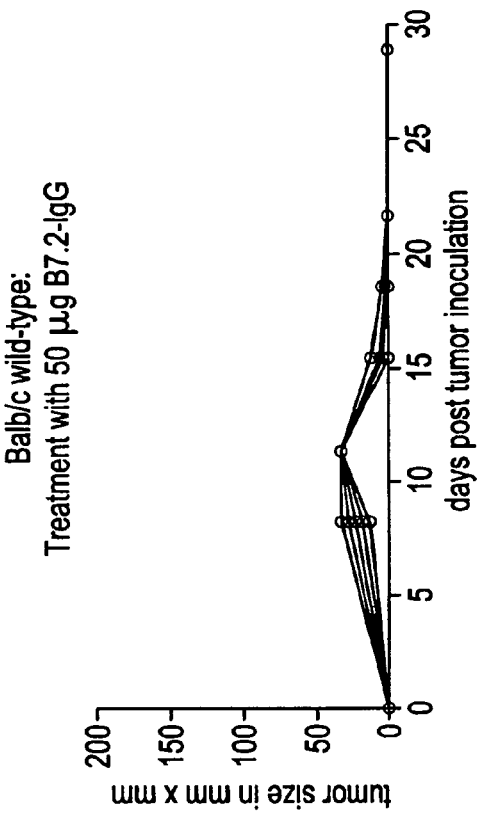
Figure 11A:
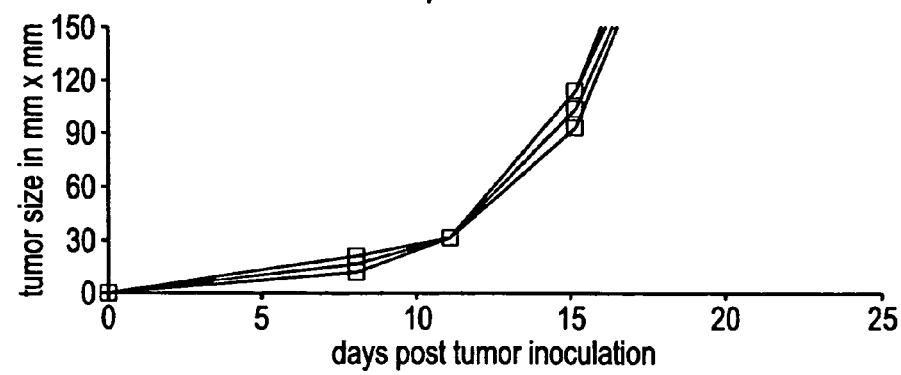
FIGS. 11 A–E is a series of line graphs indicating tumor size in tumor-bearing mice, untreated or treated with B7.2-Ig, either in wild-type mice or after depleting CD8+ or CD4+ T cells. Results indicate that CD8+, but not CD4+, T cells are required to mediate B7-IgG anti-tumor activity.
Figure 11B:
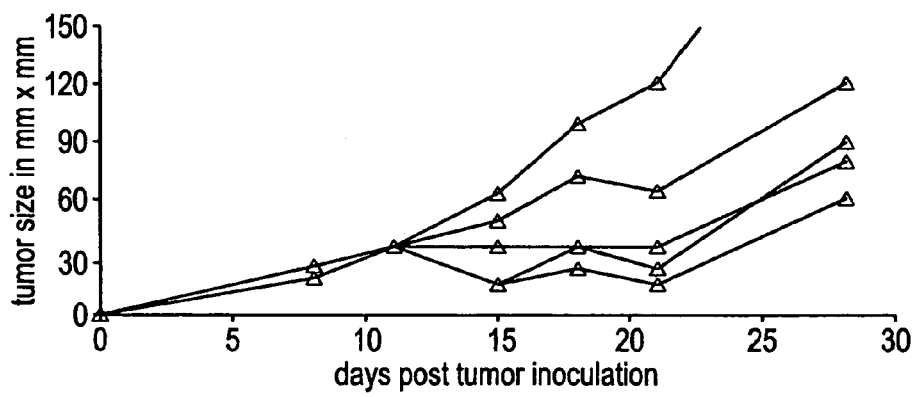
Figure 11C:
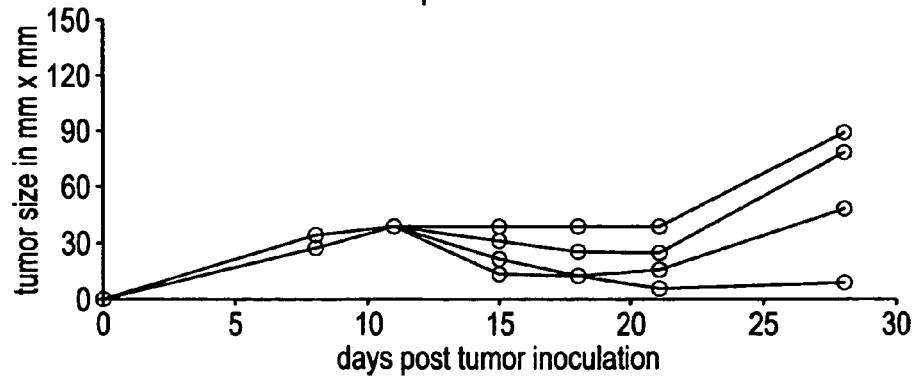
Figure 11D:
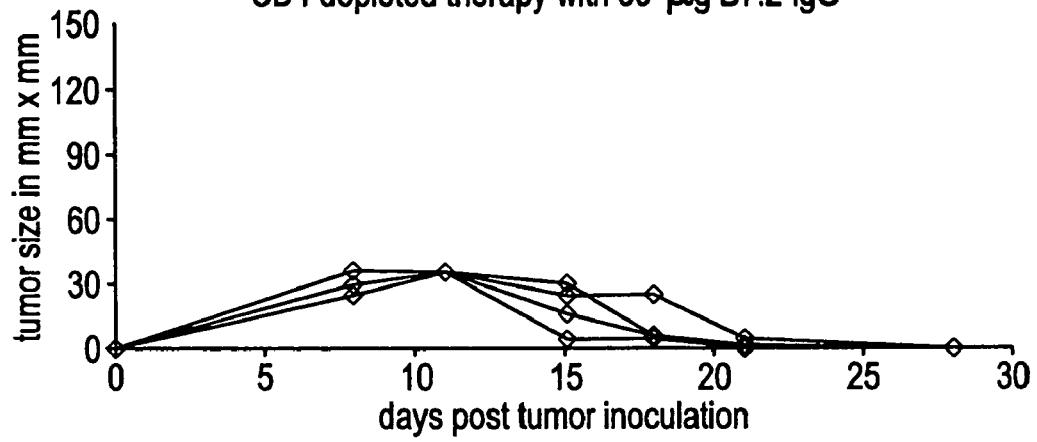
Figure 11E:
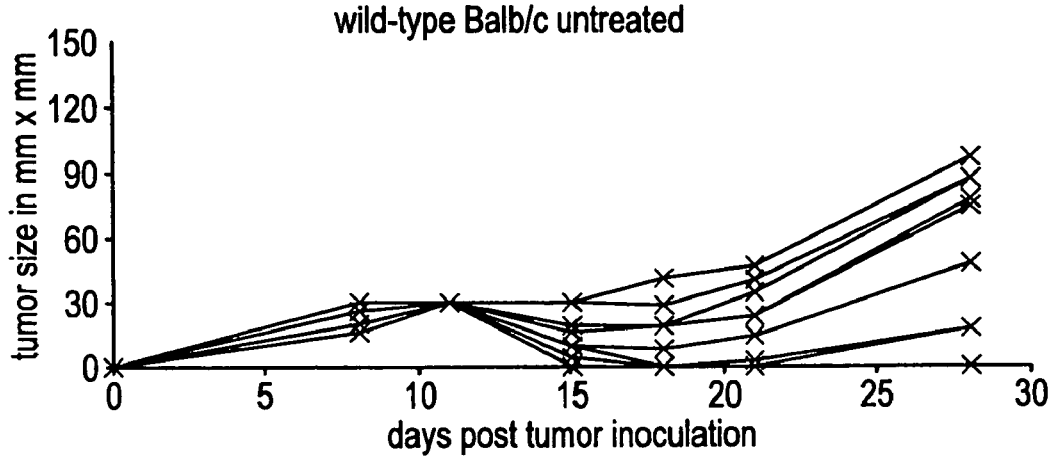
Figure 12A:
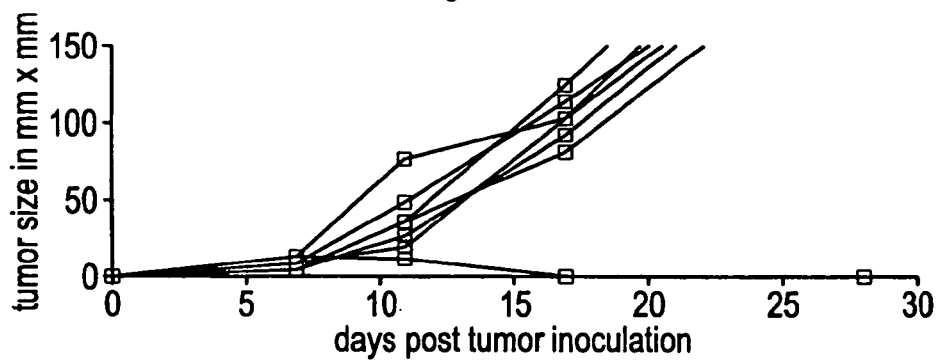
FIGS. 12 A–F is a series of line graphs indicating tumor size in Balb/c wild type or IFN-γ knockout mice with established solid tumors, knockout mice untreated (A); knockout mice treated with B7.2-IgG (B), knockout mice treated with irradiated MethA tumor cells and B7.2-IgG (C), wild-type mice untreated (D), wild type treated with B7.2-IgG (E), wild type mice treated with irradiated MethA tumor cells and B7.2IgG (F). Results indicate that B7-IgG therapy of established tumors is independent of host IFN-γ.
Figure 12B:
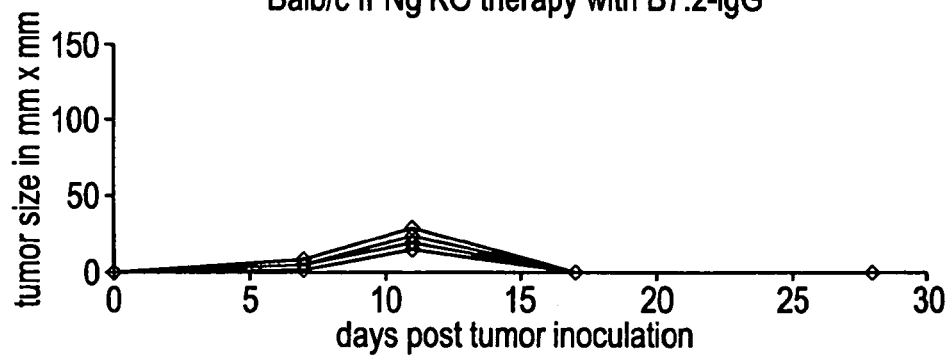
Figure 12C:
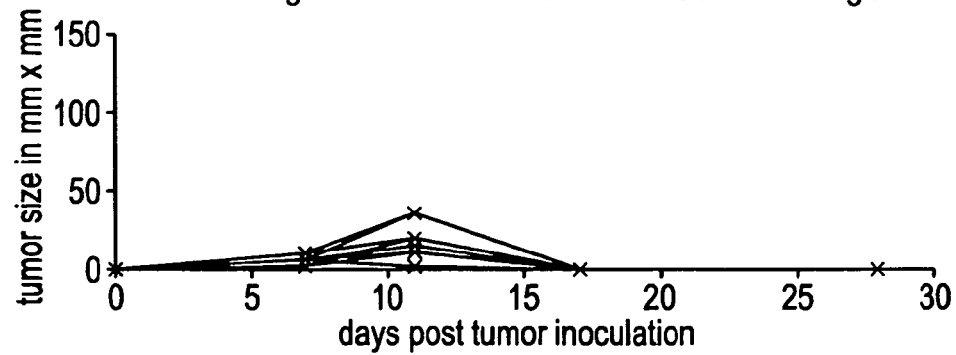
Figure 12D:
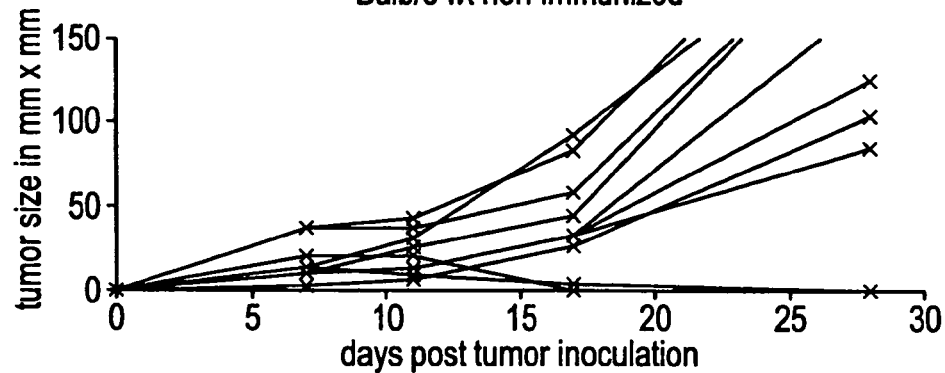
Figure 12E:
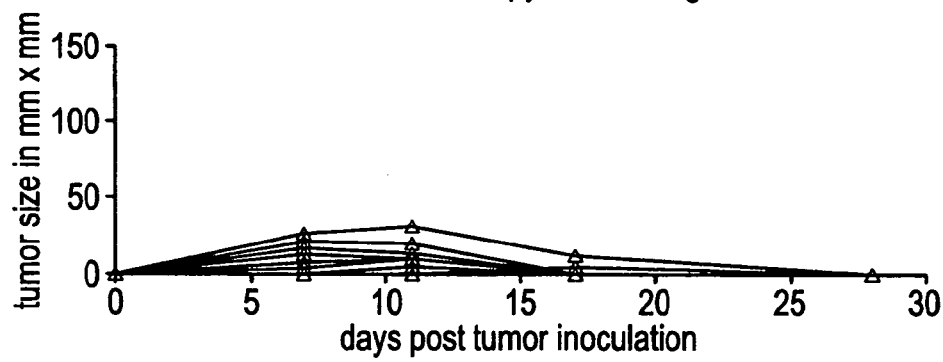
Figure 12F:
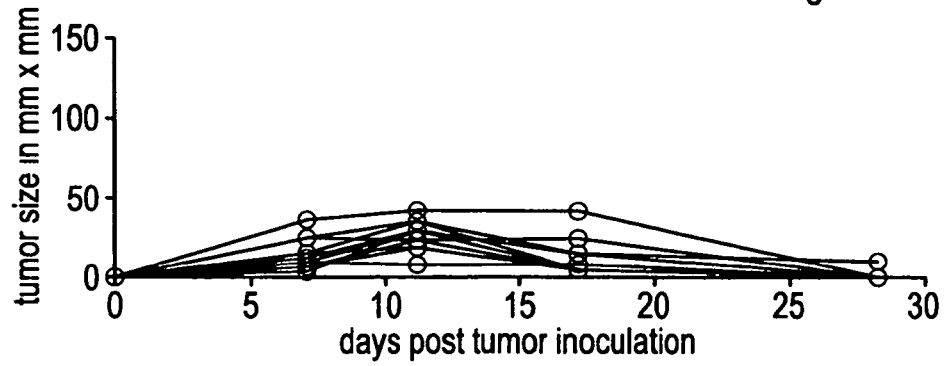

FACS® or Biocore® analyses determined that the B7-1-IgG and B7-2-IgG fusion proteins bind to murine CD28 and CTLA-4. To determine whether the B7-IgG fusion proteins would enhance or suppress T cell activation, murine splenocytes were stimulated in vitro by culturing with plate-bound anti-CD3 mAb in combination with B7-IgG immobilized on the plates. Costimulation with plate-bound anti-CD28 mAb served as a positive control. B7-1-IgG and B7-2-IgG similarly induced a dose dependent increase in proliferation and IFN-γ secretion (FIG. 5). $2 \times 10^5$ naïve splenocytes were stimulated in triplicate for 72 h with 50 ng/ml anti-CD3 monoclonal antibody and increasing amounts of immobilized anti-CD28 antibody, or B7-1 or B7-2 IgG. The proliferative response was measured by incorporation of 3H-thymidine after a 6 h pulse. Panels B and C show the amount of IFNγ or IL2 respectively, released after 72 h stimulation with 50 ng/ml anti-CD3 antibody and indicated amounts of immobilized B7-2-IgG. Cytokines were measured by standard ELISA. In the absence of anti-CD3 stimulation, B7-IgG did not induce proliferation. Immobilization or cross-linking of the B7-IgG molecules with a secondary anti-murine IgG mAb was essential for efficient costimulation, as soluble B7-IgG proteins did not enhance proliferation or IFN-γ production. B7-IgG proteins mutated in their Fc binding region (B7-1-IgG and B7-2-IgG2mut) were as effective in co-stimulating splenocytes when immobilized on the plate.

Both B7-1-IgG or B7-2-IgG Enhance the Protective Efficacy of an Irradiated Tumor Cell Vaccine The B7-IgG fusion proteins were evaluated as adjuvants in a prophylactic tumor vaccine model. Inoculation of $5 \times 10^4$ live P815 tumor cells generates a solid tumor after 5–7 days in 100% of naive DBA/2 mice. 10 DBA/2 mice per group were immunized i.fp. once with $1 \times 10^7$ irradiated P815 tumor cells. The cell vaccine was given alone or mixed with either 100 μg of B7-1-IgG, B7-2-IgG, or B7-1-IgG, B7-2-IgG mutated protein. B7-IgG was administered again on day 5. As control, 100 μg B7-1-IgG or B7-2-IgG alone was administered i.fp. on day 0 and 5. Mice were challenged with $5 \times 10^4$ live P815 tumor cells on day 7. Protection against the challenge was determined by absence of a palpable tumor after 24 days. FIG. 6 shows results from one of five representative experiments. Immunization of mice with irradiated P815 tumor cells one week before the live tumor challenge did not result in protection against tumor growth. However, a single immunization with irradiated tumor cells mixed with B7-1-IgG or B7-2-IgG induced 60–70% protection (FIG. 6, Table 2). In contrast, immunization with B7-1-IgG or B7-2-IgG alone provided no protection (FIG. 6). Protection was assessed by absence of a solid tumor after 14–24 days and/or survival for at least 60 days. The latter indicates the absence of metastatic disease.

To evaluate the role of the IgG domain for the function of the fusion proteins mice were immunized with irradiated P815 tumor cells mixed with the mutated fusion proteins, B7-IgGmut, that do not bind Fc-receptors and do not activate complement. The mutated molecules were less effective than wild type (FIG. 6, Table 2), suggesting a role for Fc binding of the B7-IgG molecules.

The efficacy of irradiated tumor cells mixed with B7-IgG's with tumor cells transfected with B7-1 or B7-2 was also compared. Vaccination with the B7-transfectants induced significantly lower anti-tumor immunity and protected only some 30% of mice, compared to 65% after immunization with irradiated wild-type P815 cells mixed with B7-IgG (Table 2). These findings indicated that B7-IgG's can be effective adjuvants for generating anti-tumor protection and may be more effective than B7-transfected tumor cells.

Vaccination with Irradiated P815 Tumor Cells Mixed with B7-1-IgG or B7-2-IgG Cured Mice of Established P815 Tumor To test the adjuvant activity of B7-IgG in a therapeutic tumor vaccine model, DBA/2 mice were injected i.d. with P815 tumor cells at a dose that generated a palpable solid tumor after five to seven days. Solid P815 tumors were established on day 0 by i.d. injection of $5 \times 10^4$ P815 cells. Vaccination started on day 7 after palpable tumors had developed. FIG. 7 shows the results of mice injected i.fp. with either PBS as control (A, E), or with irradiated P815 tumor cells alone (B) or mixed with irrelevant mouse IgG2a Ab (F), or with irradiated P815 cells mixed with B7-1 (C)— or B7-2-IgG (G). The immunization was repeated on days 7, 14, 21. PBS, irrelevant Ab, or B7-IgG, respectively was administered again three days later. Tumor growth was monitored for 40 days. After 25–30 days animals in the control groups stared to die from spontaneous metastases. Panels D and H show the survival times of the different treatment groups. Data are representative for four independent experiments. The kinetics of tumor growth and survival after vaccination are shown in FIG. 7, representative for four independent experiments. Beginning about one week after the first immunization, reduced tumor growth in the tumor regression in the groups of mice immunized with tumor cells mixed with B7-IgG was observed. Tumor growth was not reduced in groups treated with irradiated tumor cells alone or mixed with an irrelevant mouse IgG2a Ab. After three cycles of immunization with irradiated P815 tumor cells mixed with B7-IgG, the primary tumor had disappeared in 60–80% of mice. Regression of the primary tumor correlated with long-term survival of the mice. Immunization with irradiated P815 cells mixed with either B7-1-IgG or B7-2-IgG increased long-term survival to approximately 80% (FIG. 7, D, H). The majority of the mice in the untreated or irradiated tumor vaccine control groups generally died between 25 and 35 days, apparently due to spontaneous metastases formed in liver, spleen, and lymph nodes.

B7-IgGs as Therapeutic Tumor Vaccine Adjuvant in Different Tumor Models

To determine whether the results with B7-IgG were unique to the P815 tumor or the DBA/2 mouse strain, the efficacy of B7-IgGs as adjuvants in three additional tumor models in two different mouse strains was tested. Similar positive results were obtained in all four models.

Balb/c mice bearing 7-day old established MethA sarcomas were immunized with PBS, irradiated MethA cells alone, or irradiated MethA cells mixed with either B7-1-IgG or B7-2-IgG. Solid MethA or B16/F10 tumors were established in Balb/c or C57BL/6 mice, respectively. FIG. 8 shows that ten mice per group were immunized i.fp. with either irradiated tumor cells alone (B, E), or mixed with 25%1 g (C, D) or 100 μg (F, G) B7-1-IgG or B7-2-IgG, respectively. Another injection of PBS, or B7-1-IgG, B7-2-IgG, respectively, was given 3–4 days later. One group was treated with PBS alone (A, not shown for B16/F10). Tumor growth was monitored for 35 days. Mice with MethA tumors were euthanized once the tumor reached a size of 300 mm². Mice with the B16/F10 tumor were either euthanized once the tumor reached a size of 400 mm², or the animals died from a spontaneous metastases. The percent of surviving animals is shown in panel H. Experiments were repeated at least three times. Two immunizations with irradiated MethA cells mixed with B7-IgG cured 100% of mice compared to 10–15% spontaneous cures in the control groups (FIG. 8). Similar results were observed in C57BL/6 mice bearing the bladder carcinoma MB49. In C57BL/6 mice, the response of the highly metastatic and poorly immunogenic melanoma B16/F10 was also studied. Three immunizations with irradiated B16 tumor cells mixed with either of the B7-IgG proteins reduced tumor growth and improved long-term survival relative to controls (FIG. 8). The animals in the control groups all died within 35–40 days, whereas at least 40–80% of mice treated with the B7-IgG vaccine survived longer than 60 days (FIG. 8). The findings support the observations made in the P815 tumor model and demonstrate potent activity of the B7-IgGs as adjuvants for therapeutic tumor vaccine.

Therapeutic Administration of B7-IgG alone Induces Anti-Tumor Responses:

As described above, prophylactic immunization of naive mice with B7-IgGs in the absence of irradiated tumor cells did not protect mice against a tumor challenge. However, in all four therapeutic tumor models, treatment of tumor-bearing mice with B7-1-IgG or B7-2-IgG alone reduced tumor growth and increased survival (FIG. 9). Mice were inoculated with live P815 (A), MethA (B), MB49 (C), or C57BL/6 (D) tumor cells on day 0. Immunization started on days 6–8 as described. Mice were either treated with PBS (□), irradiated tumor cells alone (◇), irradiated tumor cells mixed with B7-1-IgG (Δ), or B7-2-IgG (O), or with B7-1-IgG (*) or B7-2-IgG alone (+). The mean value of tumor size for groups of 7-10 mice has been plotted. Mice were euthanized once their tumor reached a size of 400 mm² or were assigned this value if they died from metastatic disease. In all models tested, therapeutic treatment of tumor-bearing mice with B7-IgG alone slowed tumor growth, induced tumor regression and increased survival. However, data from the B 16/F 10 tumor model suggest that vaccination with irradiated tumor cells plus B7-IgG is a stronger anti-tumor treatment than therapy with B7-IgG alone, at least for poorly immunogenic tumors.

These results with soluble B7-IgG are surprising given the results obtained using costimulatory molecules presented on the surface of a cell (solid phase costimulation). Therapeutic vaccination with B7-transfected tumor cells in all three of these models was evaluated and showed no to modest effects on tumor growth and survival. The effect shown here using irradiated tumor cell vaccines mixed with soluble B7-Ig are surprisingly much stronger. Approximately $10^{16}$ B7 molecules are provided by mixing 100 μg of B7-IgG with the vaccine, compared to approximately a total of $10^{10}$–$10^{11}$ B7 molecules on the surface of $10^7$ transfected tumor cells. Such a quantitative difference may explain why vaccination with irradiated B7-transfectants is much less efficient than with live B7-transfectants where the live cells can multiply and increase the number of available B7 molecules. Other explanations may involve the extended presence of B7-IgG molecules compared to B7 molecules expressed on the surface of irradiated tumor cells. Also, the soluble molecules may distribute differently in the body and reach more appropriate sites of immune stimulation.

B7-IgG Mediated Tumor Cure is CD8 T Cell Dependent but IFN-γ Independent

To further characterize the involvement of the adaptive immune response in B7-IgG-mediated immune stimulation, B7-IgG in SCID mice that lack mature T and B cells was evaluated. Solid tumors were established in SCID mice and then they were treated with either B7-IgG alone or with an irradiated cell vaccine plus B7-IgG. Neither treatment had an effect on tumor growth, demonstrating the dependence of B7-IgG mediated tumor responses on T or B cells (FIG. 10). Tumor-bearing mice were also treated after depleting CD8 or CD4 T cells. Depletion of CD8 or CD4 T cells by antibody injection was started one day prior to initiation of B7-IgG therapy. Successful depletion was verified by FACS analysis of PBL on day 28. In CD4 depleted mice, B7-IgG induced tumor regression and cure indistinguishable from normal mice (FIG. 11), whereas CD8 depletion abrogated the B7-IgG mediated anti-tumor activity. The tumors grew slower than in CD8 depleted, untreated mice, but no tumor cure was observed (FIG. 11).

Despite the fact that IFN-γ plays an important role in anti-tumor immune surveillance and anti-tumor responses, it was determined that B7-IgG could cure established tumors independent of IFN-γ. Solid tumors were established in IFN-γ knockout mice and treated with B7-IgG or an irradiated tumor cell vaccine mixed with B7-IgG. Both treatments induced tumor regression and cure around day 28, comparable to wild-type mice, demonstrating the IFN-γ independence of B7-IgG tumor therapy (FIG. 12). Also, tumors that were not responsive to IFN-γ due to mutations of their IFN-γ receptor were still cured when treated with B7-IgG.

It was also determined that B7-IgG in anti-tumor therapy or as vaccine adjuvant is more potent than a blocking antibody to CTLA4. In three different tumor models, B7-IgG treatment cured tumors or protected against tumor challenge where an anti-CTLA4 antibody had no effect despite its much higher affinity to CTLA4 and previous reports of its blocking activity. These data demonstrate that the mechanism by which B7-IgG enhances the immune response is not solely limited to and dependent on blocking of the negative signal mediated by CTLA4.

TABLE 2

B7-IgG2a mixed with irradiated tumor cells provides protective immunity

| Immunization | Percent Protection (mean +/− SD) | Number of animals (protected/total number of animals challenged) | Number of Experiments |
|---|---|---|---|
| Naive | 8% (11) | 3/42 | 5 |
| Irradiated P815 | 2% (4) | 1/43 | 5 |
| Irradiated P815 − B7-1 transfectant | 23% (4) | 3/13 | 2 |
| Irradiated P815 + B7-1 IgG | 65% (18) | 29/45 | 4 |
| Irradiated P815 + B7-2 IgG | 60% (24) | 23/37 | 4 |
| Irradiated P815 + B7-1 IgG mutated | 28% (4) | 5/18 | 2 |
| Irradiated P815 + B7-2 IgG mutated | 20% | 2/10 | 1 |
| Irradiated P815 + anti-CD28 | 0% | 0/10 | 1 |
| Irradiated P815 + anti-CTLA-4 | 40% | 4/10 | 1 |
| Irradiated L1210-P1A | 0% (0) | 0/19 | 2 |
| Irradiated L1210-P1A + B7-1-IgGIgG | 10% (14) | 2/20 | 2 |

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method of prophylactically enhancing an immune response by a subject to an antigen comprising: administering a composition comprising a soluble, extracellular domain of a B7-1 molecule in the absence of a cross-linking agent, such that upon binding of the soluble, extracellular domain of the B7-1 molecule to its ligand, the immune response of the subject to the antigen is enhanced.

2. A method of therapeutically enhancing an immune response by a subject to an antigen comprising: administering a composition comprising a soluble, extracellular domain of a B7-1 molecule in the absence of a cross-linking agent, such that upon binding of the soluble, extracellular domain of the B7-1 molecule to its ligand, the immune response of the subject to the antigen is enhanced.

3. A method of enhancing a $CD8^+$ T cell response to a Class I-restricted antigen in a subject comprising: administering a first agent comprising a Class I-restricted antigen or fragment thereof and a composition comprising a soluble, extracellular domain of a B7-1 molecule in the absence of a cross-linking agent, such that upon administration to the subject the soluble, extracellular domain of the B7-1 molecule enhances the $CD8^+$ T cell response to the Class I-restricted antigen.

4. The method of claim 3, further comprising administering a Class II-restricted antigen to the subject.

5. The method of any of claim 1, 2, or 3, further comprising administering an adjuvant to the subject.

6. The method of any of claim 1, 2, or 3, wherein the B7-1 molecule is monospecific.

7. The method of any of claim 1, 2, or 3, wherein the B7-1 molecule is dimeric and bivalent.

8. The method of any of claim 1, 2, or 3, wherein the B7-1 molecule is monospecific and dimeric and bivalent.

9. The method of claim 8, wherein the extracellular domain of the B7-1 molecule is fused to a second protein or polypeptide comprising a portion of an immunoglobulin molecule.

10. The method of claim 9, wherein the portion of the immunoglobulin molecule comprises cysteine residues.

11. The method of claim 9, wherein the portion of the immunoglobulin molecule comprises the hinge, CH2 and CH3 regions of a human immunoglobulin molecule.

12. The method of claim 9, wherein the portion of the immunoglobulin molecule comprises the hinge, CH1, CH2 and CH3 regions of a human immunoglobulin molecule.

13. The method of claim 9, wherein the immunoglobulin molecule has been modified to reduce complement fixation and/or Fc receptor binding.

14. The method of any of claim 1, 2, or 3, wherein the antigen is a tumor cell antigen.

15. The method of claim 2, wherein the subject has a cancer of a type selected from the group consisting of: colon cancer, breast cancer, prostate cancer, renal cell cancer, leukemia, lymphoma, melanoma, mastocytoma, sarcoma, and bladder carcinoma.

16. The method of any of claim 1, 2, or 3, wherein the antigen is selected from the group consisting of: a bacterial antigen, a viral antigen, and a parasite antigen.

17. The method of any of claim 1, 2, or 3 wherein the immune response is a cellular immune response.

18. The method of any of claim 1, 2, or 3, wherein the immune response is a humoral immune response.

19. A method of prophylactically enhancing an immune response by a subject to an antigen comprising: administering a composition comprising a B7-2 fusion protein in the absence of a cross-linking agent comprising a first polypeptide which is an extracellular domain of a B7-2 molecule in soluble form, fused to a second protein or polypeptide comprising a portion of an immunoglobulin molecule, wherein the B7-2 fusion protein is monospecific, dimeric, and bivalent, such that the immune response of the subject to the antigen is enhanced.

20. A method of therapeutically enhancing an immune response by a subject to an antigen comprising: administering a composition comprising a B7-2 fission protein in the absence of a cross-linking agent, comprising a first polypeptide which is an extracellular domain of a B7-2 molecule in soluble form, fused to a second protein or polypeptide comprising a portion of an immunoglobulin molecule, wherein the B7-2 fusion protein is monospecific, dimeric, and bivalent, such that the immune response of the subject to the antigen is enhanced.

21. A method of enhancing a $CD8^+$ T cell response to a Class I-restricted antigen in a subject comprising: administering a first agent comprising a Class I-restricted antigen or fragment thereof and a composition comprising a B7-2 fusion protein in the absence of a cross-linking agent, comprising a first polypeptide which is an extracellular domain of a B7-2 molecule in soluble form, fused to a second protein or polypeptide comprising a portion of an immunoglobulin molecule, wherein the B7-2 fusion protein is monospecific, dimeric, and bivalent, such that upon administration to the subject, the $CD8^+$ T cell response to the Class I-restricted antigen is enhanced.

22. The method of any of claim 1, 2, 19, or 20, wherein the composition further comprises the antigen.

23. A method of prophylactically enhancing an immune response by a subject to an antigen, comprising: administering a composition comprising a bivalent, soluble, extracellular domain of a B7-1 molecule in the absence of a cross-linking agent, such that upon binding of the bivalent soluble, extracellular domain of the B7-1 molecule to its ligand, the immune response of the subject to the antigen is enhanced.

24. A method of therapeutically enhancing an immune response by a subject to an antigen, comprising: administering a composition comprising a bivalent, soluble, extracellular domain of a B7-1 molecule in the absence of a cross-linking agent, such that upon binding of the bivalent soluble, extracellular domain of the B7-1 molecule to its ligand, the immune response of the subject to the antigen is enhanced.

25. A method of prophylactically enhancing an immune response by a subject to an antigen, comprising: administering a composition consisting of a bivalent, soluble, extracellular domain of a B7-1 molecule in the absence of a cross-linking agent, such that the immune response of the subject to the antigen is enhanced.

26. A method of therapeutically enhancing an immune response by a subject to an antigen, comprising: administering a composition consisting of a bivalent, soluble, extracellular domain of a B7-1 molecule in the absence of a cross-linking agent, such that the immune response of the subject to the antigen is enhanced.

27. The method of claim 21, further comprising administering a Class II-restricted antigen to the subject.

28. The method of claim 21, further comprising administering an adjuvant to the subject.

29. The method of any of claims 19–21 or 23–26 wherein the antigen is a tumor cell antigen.

30. The method of any one of claim 20 or 24–26 wherein the subject has a cancer of a type selected from the group consisting of: colon cancer, breast cancer, prostate cancer, renal cell cancer, leukemia, lymphoma, melanoma, mastocytoma, sarcoma, and bladder carcinoma.

31. The method of any of claims 19–21 or 23–26, wherein the antigen is selected from the group consisting of: a bacterial antigen, a viral antigen, and a parasite antigen.

32. The method of any of claim 19, 20, or 23–26, wherein the immune response is a cellular immune response.

33. The method of any of claim 19, 20, or 23–26, wherein the immune response is a humoral immune response.

34. The method of any of claim 19, 20 or 23–26, wherein the composition further comprises the antigen.

* * * * *

SEQUENCE LISTING

<160> NUMBER OF SEQ ID NOS: 7

<210> SEQ ID NO 1
<211> LENGTH: 1491
<212> TYPE: DNA
<213> ORGANISM: Homo sapiens
<220> FEATURE:
<221> NAME/KEY: CDS
<222> LOCATION: (318)..(1181)
<221> NAME/KEY: mat_peptide
<222> LOCATION: (420)
<223> OTHER INFORMATION: Open reading frame from location 318 to 1181 bp
<223> OTHER INFORMATION: Alternate polyadenylation signal from location 1474 to 1479 bp

<400> SEQUENCE: 1

```
ccaaagaaaa agtgatttgt cattgcttta tagactgtaa gaagagaaca tctcagaagt        60
ggagtcttac cctgaaatca aaggatttaa agaaaaagtg gaattttttct tcagcaagct      120 gtgaaactaa atccacaacc tttggagacc caggaacacc ctccaatctc tgtgtgtttt       180
gtaaacatca ctggagggtc ttctacgtga gcaattggat tgtcatcagc cctgcctgtt      240
ttgcacctgg gaagtgccct ggtcttactt gggtccaaat tgttggcttt cacttttgac      300
cctaagcatc tgaagcc atg ggc cac aca cgg agg cag gga aca tca cca          350
                   Met Gly His Thr Arg Arg Gln Gly Thr Ser Pro
                                   -30                 -25 tcc aag tgt cca tac ctg aat ttc ttt cag ctc ttg gtg ctg gct ggt          398
Ser Lys Cys Pro Tyr Leu Asn Phe Phe Gln Leu Leu Val Leu Ala Gly
            -20                 -15                 -10 ctt tct cac ttc tgt tca ggt gtt atc cac gtg acc aag gaa gtg aaa          446
Leu Ser His Phe Cys Ser Gly Val Ile His Val Thr Lys Glu Val Lys
         -5                  -1   1                   5 gaa gtg gca acg ctg tcc tgt ggt cac aat gtt tct gtt gaa gag ctg          494
Glu Val Ala Thr Leu Ser Cys Gly His Asn Val Ser Val Glu Glu Leu
 10                  15                  20                  25 gca caa act cgc atc tac tgg caa aag gag aag aaa atg gtg ctg act          542
Ala Gln Thr Arg Ile Tyr Trp Gln Lys Glu Lys Lys Met Val Leu Thr
                 30                  35                  40 atg atg tct ggg gac atg aat ata tgg ccc gag tac aag aac cgg acc          590
Met Met Ser Gly Asp Met Asn Ile Trp Pro Glu Tyr Lys Asn Arg Thr
             45                  50                  55 atc ttt gat atc act aat aac ctc tcc att gtg atc ctg gct ctg cgc          638
Ile Phe Asp Ile Thr Asn Asn Leu Ser Ile Val Ile Leu Ala Leu Arg
         60                  65                  70 cca tct gac gag ggc aca tac gag tgt gtt gtt ctg aag tat gaa aaa          686
Pro Ser Asp Glu Gly Thr Tyr Glu Cys Val Val Leu Lys Tyr Glu Lys
     75                  80                  85 gac gct ttc aag cgg gaa cac ctg gct gaa gtg acg tta tca gtc aaa          734
Asp Ala Phe Lys Arg Glu His Leu Ala Glu Val Thr Leu Ser Val Lys
 90                  95                 100                 105 gct gac ttc cct aca cct agt ata tct gac ttt gaa att cca act tct          782
Ala Asp Phe Pro Thr Pro Ser Ile Ser Asp Phe Glu Ile Pro Thr Ser
                110                 115                 120 aat att aga agg ata att tgc tca acc tct gga ggt ttt cca gag cct          830
Asn Ile Arg Arg Ile Ile Cys Ser Thr Ser Gly Gly Phe Pro Glu Pro
            125                 130                 135 cac ctc tcc tgg ttg gaa aat gga gaa gaa tta aat gcc atc aac aca          878
His Leu Ser Trp Leu Glu Asn Gly Glu Glu Leu Asn Ala Ile Asn Thr
        140                 145                 150
```

-continued

```
aca gtt tcc caa gat cct gaa act gag ctc tat gct gtt agc agc aaa        926
Thr Val Ser Gln Asp Pro Glu Thr Glu Leu Tyr Ala Val Ser Ser Lys
    155                 160                 165 ctg gat ttc aat atg aca acc aac cac agc ttc atg tgt ctc atc aag        974
Leu Asp Phe Asn Met Thr Thr Asn His Ser Phe Met Cys Leu Ile Lys
170                 175                 180                 185 tat gga cat tta aga gtg aat cag acc ttc aac tgg aat aca acc aag       1022
Tyr Gly His Leu Arg Val Asn Gln Thr Phe Asn Trp Asn Thr Thr Lys
                190                 195                 200 caa gag cat ttt cct gat aac ctg ctc cca tcc tgg gcc att acc tta       1070
Gln Glu His Phe Pro Asp Asn Leu Leu Pro Ser Trp Ala Ile Thr Leu
            205                 210                 215 atc tca gta aat gga att ttt gtg ata tgc tgc ctg acc tac tgc ttt       1118
Ile Ser Val Asn Gly Ile Phe Val Ile Cys Cys Leu Thr Tyr Cys Phe
        220                 225                 230 gcc cca aga tgc aga gag aga agg agg aat gag aga ttg aga agg gaa       1166
Ala Pro Arg Cys Arg Glu Arg Arg Arg Asn Glu Arg Leu Arg Arg Glu
    235                 240                 245 agt gta cgc cct gta taacagtgtc cgcagaagca aggggctgaa aagatctgaa       1221
Ser Val Arg Pro Val
250 ggtagcctcc gtcatctctt ctgggataca tggatcgtgg ggatcatgag gcattcttcc    1281 cttaacaaat ttaagctgtt ttacccacta cctcaccttc ttaaaaacct ctttcagatt    1341 aagctgaaca gttacaagat ggctggcatc cctctccttt ctccccatat gcaatttgct    1401 taatgtaacc tcttcttttg ccatgtttcc attctgccat cttgaattgt cttgtcagcc    1461 aattcattat ctattaaaca ctaatttgag                                     1491
```

<210> SEQ ID NO 2
<211> LENGTH: 288
<212> TYPE: PRT
<213> ORGANISM: Homo sapiens
<220> FEATURE:
<223> OTHER INFORMATION: Signal sequence from location -34 to -1 : Amino
      terminal sequencing of soluble protein
<223> OTHER INFORMATION: Extracellular domain from location 1 to 208;
      Similarity with known sequence
<223> OTHER INFORMATION: Transmembrane domain from location 209 to 235;
      Similarity with known sequence
<223> OTHER INFORMATION: Intracellular domain from location 236 to 254;
      Similarity with known sequence
<223> OTHER INFORMATION: N-linked glycosylation from location 19-21,
      55-57, 64-66, 152-154, 173-175, 177-179, 192-194, 198-200,
      similarity with known sequence
<223> OTHER INFORMATION: Ig V-set domain from location 1 to 104;
      Similarity with known sequence
<223> OTHER INFORMATION: Ig C-set domain from location 105 to 202;
      Similarity with known sequence

<400> SEQUENCE: 2

```
Met Gly His Thr Arg Arg Gln Gly Thr Ser Pro Ser Lys Cys Pro Tyr
              -30                 -25                 -20

Leu Asn Phe Phe Gln Leu Leu Val Leu Ala Gly Leu Ser His Phe Cys
          -15                 -10                  -5

Ser Gly Val Ile His Val Thr Lys Glu Val Lys Glu Val Ala Thr Leu
     -1   1               5                  10

Ser Cys Gly His Asn Val Ser Val Glu Glu Leu Ala Gln Thr Arg Ile
 15                  20                  25                  30

Tyr Trp Gln Lys Glu Lys Lys Met Val Leu Thr Met Met Ser Gly Asp
                 35                  40                  45

Met Asn Ile Trp Pro Glu Tyr Lys Asn Arg Thr Ile Phe Asp Ile Thr
             50                  55                  60
```

```
Asn Asn Leu Ser Ile Val Ile Leu Ala Leu Arg Pro Ser Asp Glu Gly
             65                  70                  75

Thr Tyr Glu Cys Val Val Leu Lys Tyr Glu Lys Asp Ala Phe Lys Arg
 80                  85                  90

Glu His Leu Ala Glu Val Thr Leu Ser Val Lys Ala Asp Phe Pro Thr
 95                 100                 105                 110

Pro Ser Ile Ser Asp Phe Glu Ile Pro Thr Ser Asn Ile Arg Arg Ile
                115                 120                 125

Ile Cys Ser Thr Ser Gly Gly Phe Pro Glu Pro His Leu Ser Trp Leu
            130                 135                 140

Glu Asn Gly Glu Glu Leu Asn Ala Ile Asn Thr Thr Val Ser Gln Asp
            145                 150                 155

Pro Glu Thr Glu Leu Tyr Ala Val Ser Ser Lys Leu Asp Phe Asn Met
160                 165                 170

Thr Thr Asn His Ser Phe Met Cys Leu Ile Lys Tyr Gly His Leu Arg
175                 180                 185                 190

Val Asn Gln Thr Phe Asn Trp Asn Thr Thr Lys Gln Glu His Phe Pro
                195                 200                 205

Asp Asn Leu Leu Pro Ser Trp Ala Ile Thr Leu Ile Ser Val Asn Gly
            210                 215                 220

Ile Phe Val Ile Cys Cys Leu Thr Tyr Cys Phe Ala Pro Arg Cys Arg
            225                 230                 235

Glu Arg Arg Arg Asn Glu Arg Leu Arg Arg Glu Ser Val Arg Pro Val
240                 245                 250

<210> SEQ ID NO 3
<211> LENGTH: 1120
<212> TYPE: DNA
<213> ORGANISM: Homo sapiens
<220> FEATURE:
<221> NAME/KEY: CDS
<222> LOCATION: (107)..(1093)

<400> SEQUENCE: 3
cacagggtga aagctttgct tctctgctgc tgtaacaggg actagcacag acacacggat      60
gagtggggtc atttccagat attaggtcac agcagaagca gccaaa atg gat ccc       115
                                                  Met Asp Pro
                                                    1 cag tgc act atg gga ctg agt aac att ctc ttt gtg atg gcc ttc ctg      163
Gln Cys Thr Met Gly Leu Ser Asn Ile Leu Phe Val Met Ala Phe Leu
  5                  10                  15 ctc tct ggt gct gct cct ctg aag att caa gct tat ttc aat gag act      211
Leu Ser Gly Ala Ala Pro Leu Lys Ile Gln Ala Tyr Phe Asn Glu Thr
 20                  25                  30                  35 gca gac ctg cca tgc caa ttt gca aac tct caa aac caa agc ctg agt      259
Ala Asp Leu Pro Cys Gln Phe Ala Asn Ser Gln Asn Gln Ser Leu Ser
                 40                  45                  50 gag cta gta gta ttt tgg cag gac cag gaa aac ttg gtt ctg aat gag      307
Glu Leu Val Val Phe Trp Gln Asp Gln Glu Asn Leu Val Leu Asn Glu
             55                  60                  65 gta tac tta ggc aaa gag aaa ttt gac agt gtt cat tcc aag tat atg      355
Val Tyr Leu Gly Lys Glu Lys Phe Asp Ser Val His Ser Lys Tyr Met
         70                  75                  80 ggc cgc aca agt ttt gat tcg gac agt tgg acc ctg aga ctt cac aat      403
Gly Arg Thr Ser Phe Asp Ser Asp Ser Trp Thr Leu Arg Leu His Asn
 85                  90                  95
```

-continued

```
ctt cag atc aag gac aag ggc ttg tat caa tgt atc atc cat cac aaa        451
Leu Gln Ile Lys Asp Lys Gly Leu Tyr Gln Cys Ile Ile His His Lys
100                 105                 110                 115 aag ccc aca gga atg att cgc atc cac cag atg aat tct gaa ctg tca        499
Lys Pro Thr Gly Met Ile Arg Ile His Gln Met Asn Ser Glu Leu Ser
                120                 125                 130 gtg ctt gct aac ttc agt caa cct gaa ata gta cca att tct aat ata        547
Val Leu Ala Asn Phe Ser Gln Pro Glu Ile Val Pro Ile Ser Asn Ile
            135                 140                 145 aca gaa aat gtg tac ata aat ttg acc tgc tca tct ata cac ggt tac        595
Thr Glu Asn Val Tyr Ile Asn Leu Thr Cys Ser Ser Ile His Gly Tyr
        150                 155                 160 cca gaa cct aag aag atg agt gtt ttg cta aga acc aag aat tca act        643
Pro Glu Pro Lys Lys Met Ser Val Leu Leu Arg Thr Lys Asn Ser Thr
    165                 170                 175 atc gag tat gat ggt att atg cag aaa tct caa gat aat gtc aca gaa        691
Ile Glu Tyr Asp Gly Ile Met Gln Lys Ser Gln Asp Asn Val Thr Glu
180                 185                 190                 195 ctg tac gac gtt tcc atc agc ttg tct gtt tca ttc cct gat gtt acg        739
Leu Tyr Asp Val Ser Ile Ser Leu Ser Val Ser Phe Pro Asp Val Thr
                200                 205                 210 agc aat atg acc atc ttc tgt att ctg gaa act gac aag acg cgg ctt        787
Ser Asn Met Thr Ile Phe Cys Ile Leu Glu Thr Asp Lys Thr Arg Leu
            215                 220                 225 tta tct tca cct ttc tct ata gag ctt gag gac cct cag cct ccc cca        835
Leu Ser Ser Pro Phe Ser Ile Glu Leu Glu Asp Pro Gln Pro Pro Pro
        230                 235                 240 gac cac att cct tgg att aca gct gta ctt cca aca gtt att ata tgt        883
Asp His Ile Pro Trp Ile Thr Ala Val Leu Pro Thr Val Ile Ile Cys
    245                 250                 255 gtg atg gtt ttc tgt cta att cta tgg aaa tgg aag aag aag aag cgg        931
Val Met Val Phe Cys Leu Ile Leu Trp Lys Trp Lys Lys Lys Lys Arg
260                 265                 270                 275 cct cgc aac tct tat aaa tgt gga acc aac aca atg gag agg gaa gag        979
Pro Arg Asn Ser Tyr Lys Cys Gly Thr Asn Thr Met Glu Arg Glu Glu
                280                 285                 290 agt gaa cag acc aag aaa aga gaa aaa atc cat ata cct gaa aga tct       1027
Ser Glu Gln Thr Lys Lys Arg Glu Lys Ile His Ile Pro Glu Arg Ser
            295                 300                 305 gat gaa gcc cag cgt gtt ttt aaa agt tcg aag aca tct tca tgc gac       1075
Asp Glu Ala Gln Arg Val Phe Lys Ser Ser Lys Thr Ser Ser Cys Asp
        310                 315                 320 aaa agt gat aca tgt ttt taattaaaga gtaaagccca aaaaaa                  1120
Lys Ser Asp Thr Cys Phe
    325
```

<210> SEQ ID NO 4
<211> LENGTH: 329
<212> TYPE: PRT
<213> ORGANISM: Homo sapiens

<400> SEQUENCE: 4

```
Met Asp Pro Gln Cys Thr Met Gly Leu Ser Asn Ile Leu Phe Val Met
1               5                   10                  15

Ala Phe Leu Leu Ser Gly Ala Ala Pro Leu Lys Ile Gln Ala Tyr Phe
            20                  25                  30

Asn Glu Thr Ala Asp Leu Pro Cys Gln Phe Ala Asn Ser Gln Asn Gln
        35                  40                  45

Ser Leu Ser Glu Leu Val Val Phe Trp Gln Asp Gln Glu Asn Leu Val
    50                  55                  60
```

-continued

```
Leu Asn Glu Val Tyr Leu Gly Lys Glu Lys Phe Asp Ser Val His Ser
 65                  70                  75                  80

Lys Tyr Met Gly Arg Thr Ser Phe Asp Ser Asp Ser Trp Thr Leu Arg
                 85                  90                  95

Leu His Asn Leu Gln Ile Lys Asp Lys Gly Leu Tyr Gln Cys Ile Ile
            100                 105                 110

His His Lys Lys Pro Thr Gly Met Ile Arg Ile His Gln Met Asn Ser
        115                 120                 125

Glu Leu Ser Val Leu Ala Asn Phe Ser Gln Pro Glu Ile Val Pro Ile
    130                 135                 140

Ser Asn Ile Thr Glu Asn Val Tyr Ile Asn Leu Thr Cys Ser Ser Ile
145                 150                 155                 160

His Gly Tyr Pro Glu Pro Lys Lys Met Ser Val Leu Arg Thr Lys
                165                 170                 175

Asn Ser Thr Ile Glu Tyr Asp Gly Ile Met Gln Lys Ser Gln Asp Asn
            180                 185                 190

Val Thr Glu Leu Tyr Asp Val Ser Ile Ser Leu Ser Val Ser Phe Pro
        195                 200                 205

Asp Val Thr Ser Asn Met Thr Ile Phe Cys Ile Leu Glu Thr Asp Lys
    210                 215                 220

Thr Arg Leu Leu Ser Ser Pro Phe Ser Ile Glu Leu Glu Asp Pro Gln
225                 230                 235                 240

Pro Pro Pro Asp His Ile Pro Trp Ile Thr Ala Val Leu Pro Thr Val
                245                 250                 255

Ile Ile Cys Val Met Val Phe Cys Leu Ile Leu Trp Lys Trp Lys Lys
            260                 265                 270

Lys Lys Arg Pro Arg Asn Ser Tyr Lys Cys Gly Thr Asn Thr Met Glu
        275                 280                 285

Arg Glu Glu Ser Glu Gln Thr Lys Lys Arg Glu Lys Ile His Ile Pro
    290                 295                 300

Glu Arg Ser Asp Glu Ala Gln Arg Val Phe Lys Ser Ser Lys Thr Ser
305                 310                 315                 320

Ser Cys Asp Lys Ser Asp Thr Cys Phe
                325

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Peptide

<400> SEQUENCE: 5

Thr Tyr Gln Arg Thr Arg Ala Leu Val
  1               5

<210> SEQ ID NO 6
<211> LENGTH: 23
<212> TYPE: PRT
<213> ORGANISM: Artificial Sequence
<220> FEATURE:
<223> OTHER INFORMATION: Description of Artificial Sequence: Peptide

<400> SEQUENCE: 6

Arg Leu Ile Gln Asn Ser Leu Thr Ile Glu Arg Met Val Leu Ser Ala
  1               5                  10                  15

Phe Asp Glu Arg Arg Asn Lys
                 20
```

-continued

```
<210> SEQ ID NO 7
<211> LENGTH: 24
<212> TYPE: PRT
<213> ORGANISM: Artificial Sequence
<220> FEATURE:
<223> OTHER INFORMATION: Description of Artificial Sequence: Peptide

<400> SEQUENCE: 7

Phe Trp Arg Gly Glu Asn Gly Arg Lys Thr Arg Ile Ala Tyr Glu Arg
  1               5                  10                  15

Met Cys Asn Ile Leu Lys Gly Lys
                20
```